United States Patent [19]

DiNinno et al.

[11] Patent Number: 5,153,186
[45] Date of Patent: Oct. 6, 1992

[54] 2-BENZOCOUMARINYL-CARBAPENEMS

[75] Inventors: Frank DiNinno, Old Bridge; Thomas A. Rano, Somerville; Mark L. Greenlee, Rahway, all of N.J.

[73] Assignee: Merck & Co., Inc., Rahway, N.J.

[21] Appl. No.: 705,239

[22] Filed: May 24, 1991

[51] Int. Cl.$^5$ .................... C07D 487/04; A61K 31/40
[52] U.S. Cl. ..................................... 514/210; 540/302
[58] Field of Search ......................... 540/302; 514/210

[56] References Cited

U.S. PATENT DOCUMENTS

| | | | |
|---|---|---|---|
| 4,260,627 | 4/1981 | Christensen et al. | 424/274 |
| 4,465,632 | 8/1984 | Christensen et al. | 260/245.2 |
| 4,543,257 | 9/1985 | Cama et al. | 514/210 |
| 4,729,993 | 3/1988 | Christensen et al. | 514/210 |
| 4,775,669 | 10/1988 | Cama et al. | 514/210 |
| 4,962,101 | 10/1990 | DiNinno et al. | 514/210 |
| 4,978,659 | 8/1989 | DiNinno et al. | 514/210 |
| 5,004,739 | 4/1991 | Salzmann et al. | 514/210 |
| 5,004,740 | 4/1991 | Salzmann et al. | 514/210 |
| 5,006,519 | 4/1991 | DiNinno et al. | 514/210 |
| 5,011,832 | 4/1991 | Salzmann et al. | 514/210 |
| 5,025,006 | 6/1991 | Salzmann et al. | 514/210 |
| 5,025,007 | 6/1991 | Greenlee et al. | 514/210 |
| 5,025,008 | 6/1991 | DiNinno et al. | 514/210 |
| 5,032,587 | 7/1991 | DiNinno et al. | 514/210 |
| 5,034,384 | 7/1991 | Greenlee et al. | 514/210 |
| 5,034,385 | 7/1991 | DiNinno et al. | 514/210 |
| 5,037,820 | 8/1991 | DiNinno et al. | 514/210 |

OTHER PUBLICATIONS

L. D. Cama et al., Total Synthesis of Thienamycin Analogs-III Tetrahedron 39, 2531 (1983).
R. N. Guthikonda et al., Structure Activity Relationship in the 2-Arylcarbapenem Series, J. Med. Chem., 30, 871 (1987).

Primary Examiner—Robert Gerstl
Attorney, Agent, or Firm—Curtis C. Panzer; Raymond M. Speer

[57] ABSTRACT

Carbapenems of the formula

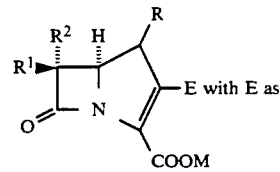

with E as

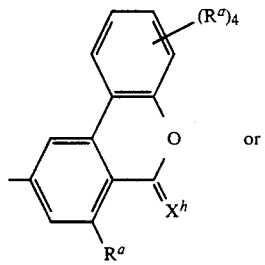

or

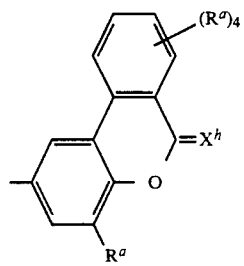

are useful antibacterial agents.

22 Claims, No Drawings

2-BENZOCOUMARINYL-CARBAPENEMS

BACKGROUND OF THE INVENTION

The present invention relates to antibacterial agents of the carbapenem class, in which the 2-position sidechain is characterized by a benzocoumarin moiety, substituted by various cationic and neutral substituents, as described in more detail further below.

Thienamycin was an early carbapenem antibacterial agent having a broad spectrum; it has the following formula:

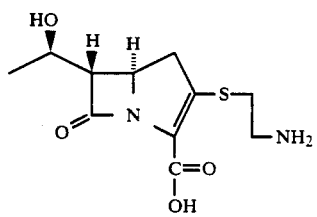

Later, N-formimidoyl thienamycin was discovered; it has the formula:

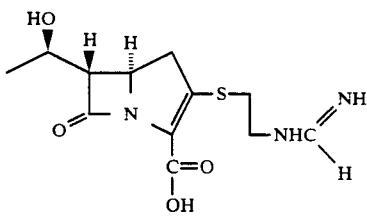

The 2-benzocoumarinyl-carbapenems of the present invention are not characterized by a broad antibacterial spectrum such as that of thienamycin or N-formimidoyl thienamycin. Rather, their spectrum of activity is largely limited to gram positive microorganisms, especially methicillin resistant *Staphylococcus aureus* (MRSA), methicillin resistant *Staphylococcus epidermidis* (MRSE), and methicillin resistant coagulase negative Staphylococci (MRCNS). The antibacterial compounds of the present invention thus comprise an important contribution to therapy of these difficult to control pathogens. Moreover, there is an increasing need for agents effective against such pathogens (MRSA/MRCNS) which are at the same time safe, i.e., free from undesirable toxic side effects. No β-lactam antibacterial has yet been found which meets these requirements. And, the current agent of choice, vancomycin, a glycopeptide antibacterial, is experiencing an ever increasing amount of resistance in the MRSA/MRCNS pathogens.

More recently, carbapenem antibacterial agents have been described which have a 2-substituent which is an aryl moiety optionally substituted by, e.g., aminomethyl and substituted aminomethyl. These agents are described in U.S. Pat. Nos. 4,543,257 and 4,260,627 and have the formula:

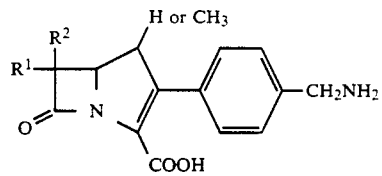

However, there is no description or suggestion of a benzocoumarinyl 2-substituent such as characterizes the compounds of the present invention, nor is there any suggestion of the surprisingly better anti-MRSA/MRCNS activity of the compounds of the present invention.

U.S. Pat. No. 4,978,659 describes a particular class of compounds of the formula:

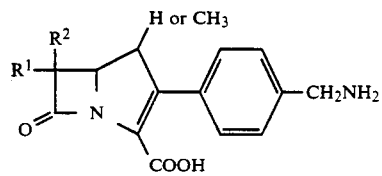

but this limited teaching in no way suggests the totally different compounds of the present invention, nor their surprisingly better anti-MRSA/MRCNS activity.

SUMMARY OF INVENTION

The present invention provides novel carbapenem compounds of the formula:

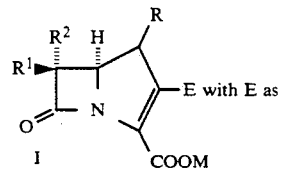

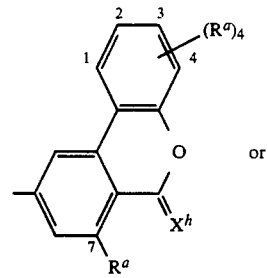

or

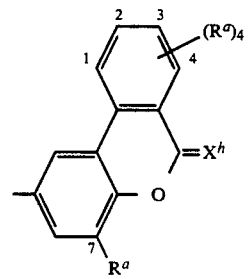

wherein:
R is H or $CH_3$;
$R^1$ and $R^2$ are independently H, $CH_3-$, $CH_3CH_2-$, $(CH_3)_2CH-$, $HOCH_2-$, $CH_3CH(OH)-$, $(CH_3)_2C(OH)-$, $FCH_2CH(OH)-$, $F_2CHCH(OH)-$, $F_3CCH(OH)-$, $CH_3CH(F)-$, $CH_3CF_2-$, or $(CH_3)_2C(F)-$;

$X^h$ is O or S;

$R^a$ are independently selected from the group consisting of hydrogen and the radicals set out below, provided that one but not more than one $R^a$ is a Type I substituent, the remaining non-hydrogen substituents being selected from Type II, and in total not more than four $R^a$ radicals are other than hydrogen:

I

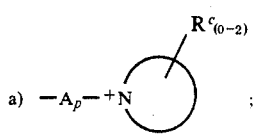

a) $-A_p-{}^+N$ ;

where

A is $(CH_2)_m-Q-(CH_2)_n$, where m is 0 to 6 and n is 1 to 6 and Q is a covalent bond, O, S, SO, $SO_2$, NH, $-SO_2NH-$, $-NHSO_2-$, $-CONH-$, $-NHCO-$, $-SO_2N(C_1-C_4alkyl)-$, $-N(C_1-C_4alkyl)SO_2-$, $-CON(C_1-C_4alkyl)-$, $-N(C_1-C_4alkyl)CO-$, $-CH=CH-$, $-CO-$, $-OC(O)-$, $-C(O)O-$ or $N(C_1-C_4alkyl)$ and $(CH_2)_m$ is attached to the benzocoumarinyl moiety;

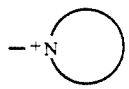

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to from the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is $R^a$ as defined under II below, hydrogen, or $-NR^yR^z$ (where $R^y$ and $R^z$ are defined in II below), but independently selected from $R^a$ and from each other if more than one $R^c$ is present, and is attached to a carbon ring atom or a nitrogen heteroatom the valency of which is not satisfied by the ring bonds;

p is 0 or 1;

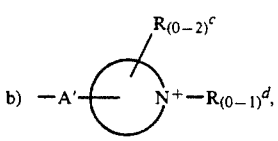

b) $-A'-$ $N^+-R_{(0-1)}{}^d$, where

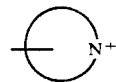

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent $R^d$ in addition to the ring bonds thereto, with said first nitrogen neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1-C_4alkyl$ (where the alkyl group is optionally mono-substituted with $R^q$ as defined under IIc below);

A' is $(CH_2)_m-Q-(CH_2)_n$, where m is 0 to 6 and n is 0 to 6 and Q is given above;

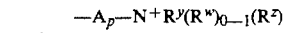

$-A_p-N^+R^y(R^w)_{0-1}(R^z)$  c)

where $R^y$ and $R^z$ are as defined under II below, $R^y$ and $R^z$ may further be together a $C_2-C_4$ alkylidene radical to form a ring (optionally mono-substituted with $R^q$ as defined below) interrupted by $N(O)R^e$ or $N^+(R^e)_2$ (where $R^e$ is hydrogen, $C_1-C_4$ alkyl, or $C_1-C_4$ alkyl mono-substituted with $R^q$ as defined below), $R^w$ is hydrogen, $C_{1-4}$ alkyl, $O^-$, $NH_2$, or absent in which case the nitrogen is neutral, $R^w$, $R^y$ and $R^z$ may further together form a $C_5-C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+-O^-$, p is 0 or 1, and A is as defined above;

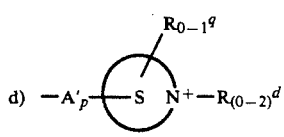

d) $-A'_p-$ $S$ $N^+-R_{(0-2)}{}^d$ where

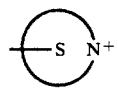

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), S(O)$_2$ and NR$^e$ where R$^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$-$C_4$alkyl;

A' is defined above; and p is defined above;

$R^q$ is defined below;

II a) a trifluoromethyl group: —CF$_3$;

b) a halogen atom: —Br, —Cl, —F, or —I;

c) $C_1$-$C_4$ alkoxy radical: —OC$_{1-4}$ alkyl, wherein the alkyl is optionally mono-substituted by $R^q$, where $R^q$ is a member selected from the group consisting of —OH, —OCH$_3$, —CN, —C(O)NH$_2$, —OC(O)NH$_2$, CHO, —OC(O)N(CH$_3$)$_2$, —SO$_2$NH$_2$, —SO$_2$N(CH$_3$)$_2$, —SOCH$_3$, —SO$_2$CH$_3$, —F, —CF$_3$, —COOM$^a$ (where M$^a$ is hydrogen, alkali metal, methyl or phenyl), tetrazolyl (where the point of attachment is the carbon atom of the tetrazole ring and one of the nitrogen atoms is mono-substituted by M$^a$ as defined above) and —SO$_3$M$^b$ (where M$^b$ is hydrogen or an alkali metal);

d) a hydroxy group: —OH;

e) a carbonyloxy radical: —O(C=O)R$^s$, where

R$^s$ is $C_{1-4}$ alkyl or phenyl, each of which is optionally mono-substituted by R$^q$ as defined above or tri-substituted with —F;

f) a carbamoyloxy radical: —O(C=O)N(R$^y$)R$^z$ where R$^y$ and R$^z$ are independently H, $C_{1-4}$ alkyl (optionally mono-substituted by R$^q$ as defined above), together a 3- to 5-membered alkylidene radical to form a ring (optionally substituted with R$^q$ as defined above) or together a 2- to 4-membered alkylidene radical, interrupted by —O—, —S—, —S(O)— or —S(O)$_2$— to form a ring (where the ring is optionally mono-substituted with Rq as defined above);

g) a sulfur radical: —S(O)$_n$—R$^s$ where n=0–2, and R$^s$ is defined above;

h) a sulfamoyl group: —SO$_2$N(R$^y$)R$^z$ where R$^y$ and R$^z$ are as defined above;

i) azido: N$_3$ j) a formamido group: —N(R$^t$) (C=O)H, where R$^t$ is is H or $C_{1-4}$ alkyl, and the alkyl thereof is optionally mono-substituted by R$^q$ as defined above;

k) a ($C_1$-$C_4$ alkyl)carbonylamino radical: —N(R$^t$)(C=O)C$_{1-4}$ alkyl, where R$^t$ is as defined above, and the alkyl group is also optionally mono-substituted by R$^q$ as defined above;

l) a ($C_1$-$C_4$ alkoxy) carbonylamino radical: —N(R$^t$)(C=O)OC$_{1-4}$ alkyl, where R$^t$ is as defined above, and the alkyl group is also optionally mono-substituted by R$^q$ as defined above;

m) a ureido group: —N(R$^t$) (C=O)N(R$^y$)R$^z$ where R$^t$, R$^y$ and R$^z$ are as defined above;

n) a sulfonamido group: —N(R$^t$)SO$_2$R$^s$, where R$^s$ and R$^t$ are as defined above;

o) a cyano group: —CN;

p) a formyl or acetalized formyl radical: —(C=O)H or —CH(OCH$_3$)$_2$;

q) ($C_1$-$C_4$ alkyl)carbonyl radical wherein the carbonyl is acetalized: —C(OCH$_3$)$_2$C$_{1-4}$ alkyl, where the alkyl is optionally mono-substituted by R$^q$ as defined above;

r) carbonyl radical: —(C=O)R$^s$, where R$^s$ is as defined above;

s) a hydroximinomethyl radical in which the oxygen or carbon atom is optionally substituted by a $C_1$-$C_4$ alkyl group: —(C=NOR$^z$)R$^y$ where R$^y$ and R$^z$ are as defined above, except they may not be joined together to form a ring;

t) a ($C_1$-$C_4$ alkoxy)carbonyl radical: —(C=O)OC$_{1-4}$ alkyl, where the alkyl is optionally mono-substituted by R$^q$ as defined above;

u) a carbamoyl radical: —(C=O)N(R$^y$)R$^z$ where R$^y$ and R$^z$ are as defined above;

v) an N-hydroxycarbamoyl or N($C_1$-$C_4$ alkoxy)carbamoyl radical in which the nitrogen atom may be additionally substituted by a $C_1$-$C_4$ alkyl group: —(C=O)—N(OR$^y$)R$^z$ where R$^y$ and R$^z$ are as defined above, except they may not be joined together to form a ring;

w) a thiocarbamoyl group: —(C=S)N(R$^y$)(R$^z$) where R$^y$ and R$^z$ are as defined above;

x) carboxyl: —COOM$^b$, where M$^b$ is as defined above;

y) thiocyanate: —SCN;

z) trifluoromethylthio: —SCF$_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by R$^q$ as defined above;

ab) an anionic function selected from the group consisting of: phosphono [P=O(OM$^b$)$_2$]; alkylphosphono {P=O(OM$^b$)—[O($C_1$-$C_4$ alkyl)]}; alkylphosphinyl [P=O(OM$^b$)—($C_1$-$C_4$alkyl)]; phosphoramido [P=O(OM$^b$)N(R$^y$)R$^z$ and P=O(OM$^b$)NHR$^x$]; sulfino (SO$_2$M$^b$); sulfo (SO$_3$M$^b$); acylsulfonamides selected from the structures CONM$^b$SO$_2$R$^x$, CONM$^b$SO$_2$N(R$^y$)R$^z$, SO$_2$NM$^b$CON(R$^y$)R$^z$; and SO$_2$NM$^b$CN, where R$^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by R$^q$, as defined above; M$^b$ is as defined above; and R$^y$ and R$^z$ are as defined above;

ac) $C_5$-$C_7$ cycloalkyl group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2-C_4$ alkenyl radical, optionally mono-substituted by one of the substituents a) to ac) above and phenyl which is optionally substituted by $R^q$ as defined above;

ae) $C_2-C_4$ alkynyl radical, optionally mono-substituted by one of the substituents a) to ac) above;

af) $C_1-C_4$ alkyl radical;

ag) $C_1-C_4$ alkyl mono-substituted by one of the substituents a)-ac) above;

ah) a 2-oxazolidinonyl moiety in which the point of attachment is the nitrogen atom of the oxazolidinone ring, the ring oxygen atom is optionally replaced by a heteroatom selected from —S— and $NR^t$ (where $R^t$ is as defined above) and one of the saturated carbon atoms of the oxazolidinone ring is optionally mono-substituted by one of the substituents a) to ag) above; and M is selected from:
i) hydrogen;
ii) a pharmaceutically acceptable esterifying group or removable carboxyl protecting group;
iii) an alkali metal or other pharmaceutically acceptable cation; or
iv) a negative charge which is balanced by a positively charged group.

The present invention also provides novel carbapenem intermediates of the formula:

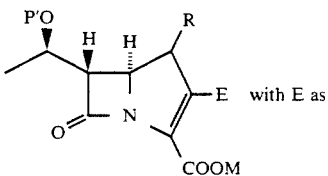

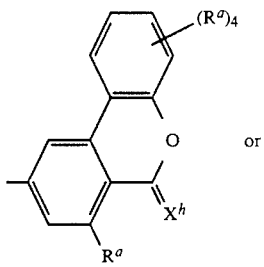

or

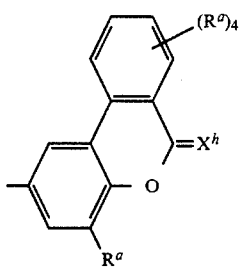

wherein:
R is H or $CH_3$;
$X^h$ is O or S;
$R^a$ is defined above, with the proviso that $R^q$ additionally includes $OP'$ where $P'$ is defined below, that $M^a$ and $M^b$ of $R^q$ both include M and that the Type d) hydroxy substituent additionally may be protected hydroxy, $OP'$;
$P'$ is a removable protecting group for hydroxy; and M is a removable protecting group for carboxy; and the Type I, $R^a$ substituent is balanced with the anionic form of Z where Z is methanesulfonyloxy, trifluoromethanesulfonyloxy, fluorosulfonyloxy, p-toluenesulfonyloxy, 2,4,6-triisopropylbenzenesulfonyloxy, p-bromobenzenesulfonyloxy, p-nitrobenzenesulfonyloxy, bromo and iodo. Preferred intermediates have the formula:

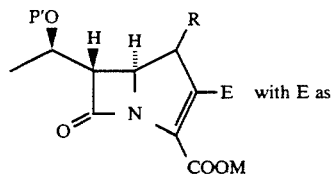

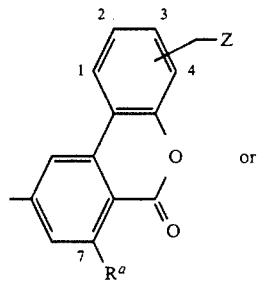

or

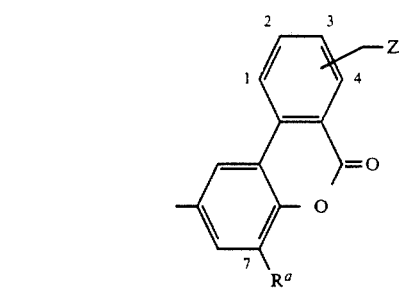

wherein
R is —H or —$CH_3$;
$R^a$ is selected from the group consisting of H, $OP'$, Cl, Br, I, $SCH_3$, CN, CHO, $SOCH_3$, $SO_2CH_3$, $CO_2M$, $CH_2OP'$ or $CONH_2$;
$P'$ is a removable protecting group for hydroxy;
M is a removable protecting group for carboxy; and
Z is selected from the group consisting of alkylsulfonyloxy, substituted alkylsulfonyloxy, arylsulfonyloxy, substituted arylsulfonyloxy, fluorosulfonyloxy, and halogen; and with the proviso that the —$CH_2$—Z moiety is in the 3-or 4-position of the benzocoumarin as numbered above.

DETAILED DESCRIPTION OF THE INVENTION

The manufacture of compounds of Formula I may be carried out in a three-stage synthesis scheme followed by a final step which allows for the removal of any protecting groups. The objective of the first synthetic stage is to produce a base benzocoumarin compound which may be converted to the two-position substituent of the carbapenem of Formula I. The objective of the second synthetic stage is to attach the base benzocoumarin to the carbapenem. Finally, the objective of the third synthetic stage is to substitute the benzocoumarin with the desired $R^a$. This third synthetic stage may be performed after the first synthetic stage or during or after the second synthetic stage according to the nature of the various $R^a$.

Flow Sheets A1 and A2 demonstrate a suggested first stage synthesis. Flow Sheets B and C demonstrate two alternative second stage syntheses. The third synthesis varies according to the selected $R^a$.

The suggested first synthesis herein, Flow Sheets A1 and A2, can be generally described as a directed ortho metalation reaction to prepare starting materials required for a Suzuki cross-coupling reaction and finally ring closure to produce the desired benzocoumarin platform. This suggested first synthesis is utilized to produce similar benzocoumarin compounds by Snieckus, V., *Chem. Rev.* 1990, 90, 879-933; Sharp, M. J. and Sniekus, V., *Tetrahedron Lett.*, 1985, 26, 5977-6000. A similar production of biaryls and phenanthridones may be analogously applied to benzocoumarins and is described by Fu, J. M. and Snieckus, V., *Tetrahedron Lett.* 1990, 31, 1665; Siddiqui, M. A., et al., *Tetrahedron Lett.*, 1988, Vol. 29, 5463-5466; Mills, R. J., et al., *J. Org. Chem.*, 1989, 54, 4372-4385; and Suzuki, A., et al., *Syn. Comm.*, 1981, 11, 513-519.

Referring to Flow Sheet A1 compound A1-1 is substituted with a directed metalation group (DMG) by methods according to Snieckus, et al., above. The function of the directed metalation group (DMG) is to orchestrate adornment of the aromatic ring. It is highly desirable of the DMG that it also provide a precursor substituent for the necessary carboxy function or phenolic function forming the lactone linkage of the object benzocoumarin. Suitable DMG to serve as a carboxyl precursor are secondary and tertiary amides and oxazolino groups. Specifically these precursors may be, for example, —CONEt$_2$, —CONHMe, 4,4-dimethyl-2-oxazolinyl, and the like. In the instance of compound A1-1, DMG is of the carboxyl precursor type. Suitable DMG to serve as a phenolic precursor are carbamates and ethers. Specifically, these precursors may be O-methoxymethyl (OMOM), OMe, OCONEt$_2$, 2-(trimethylsilyl)ethoxymethoxy (OSEM) and the like. Compound A2-1 as described below is by way of example, of the phenolic precursor type.

As the first step of flow Sheet A1, the bromine of compound A1-1 is protected through silylation via halogen metal exchange in the presence of trimethylsilyl chloride (TMS-Cl) at between about −100° to −50° C. to produce aryl silane A1-2. Incorporation of an ortho substitutent $R^a$ or its appropriate precursor may be made on compound A1-2 in accordance with standard directed metalation procedures described by Snieckus, et al., above. The resultant substituted aryl silane A1-3 is iteratively ortho metalated and treated with an appropriate boron containing electrophile to obtain the requisite aryl boronic acid A1-4. Suitable boron containing electrophiles include lower alkyl borates, such as trimethyl borate and tri-i-propyl borate. Alternatively, and not shown in the Flow Sheets, the ortho metalated compound may be treated with electrophiles such as trialkyltin halides providing the corresponding aryl stannanes which in turn are also useful intermediates in the production of biphenyls as reported by Stille, et al., *J. Am. Chem. Soc.*, 1987, 109, 5478-5486. Preparation of biphenyl intermediate A1-6 is accomplished in the Flow Sheets utilizing the Suzuki cross-coupling procedure and the appropriately adorned aryl compounds A1-4 and A1-5. The Suzuki coupling can be generally described as the reaction of an aryl boronic acid with an aryl halide or halide equivalent employing tetrakis(triphenylphosphine) palladium(0) catalyst in the presence of an aqueous solution of sodium carbonate in the solvents toluene/ethanol. The resulting biphenyl compound is isolated by standard methods. Compound A1-5 may itself be produced by standard methods to obtain the halogen substitution, X″, the phenolic moiety, —OR′, and the desired substituents $R^a$ or their precursors. The preferred halogen X″ is bromine, iodine or the halogen equivalent trifluoromethanesulfonyloxy. The preferred phenolic moiety, —OR′, may be any of the oxygen based DMGs described above, or a suitably protected phenol where the protecting group is not a DMG. Biphenyl compound A1-6 is subsequently transformed into the halogenated biphenyl A1-7 via ipso substitution of the trimethylsilyl moiety in methylene chloride or other appropriate solvent employing iodine monochloride. Any number of halogenating reagents are suitable, such as IBr, NBS, I$_2$, Br$_2$, etc., which must be compatible with the already existing functionalities. Finally, the object compound, B1-1, is obtained via lactonization of the phenolic moiety with the latent carboxy precursor in the form of DMG.

Referring to Flow Sheet A2, the regioisomeric benzocoumarin B1-2, may be produced in a manner analogous to that of benzocoumarin B1-1. Compound A2-1 is dissimilar to compound A1-4 in that DMG of compound A2-1 is of the phenolic precursor type. Compound A2-1 is reacted with the appropriately adorned compound A2-2 to prepare biphenyl intermediate A2-3 utilizing the Suzuki cross-coupling procedure. As above biphenyl compound A2-3 is transformed into halogenated biphenyl via ipso substitution on A2-4 and finally into object benzocoumarin B1-2 via lactonization.

Presented with Flow Sheet A1 and A2, the skilled artisan will appreciate certain modifications as possibly beneficial. In one modification, the ipso substitution of silicon to halogen might be performed after cyclization to form the object benzocoumarin. In another modification, compounds A1-5 and A2-2 may be adorned utilizing a DMG substitutent replacing —OR′ and —CO$_2$Me respectively. As above, the DMG substituent directs adornment of $R^a$ or precursors thereof in manufacture. As above, the DMG should be of the carboxyl precursor type or phenolic precursor type as appropriate. In yet another modification, the oxocarbonyl of intermediate B1-1 or B1-2 can be converted to a thiocarbonyl to produce $X^h$ as S using Lawesson type reagents or by treating with phosphorus pentasulfide in an appropriate solvent. Another modification to produce $X^h$ as S is to employ a carbon based DMG wherein the oxocarbonyl moiety is replaced by thiocarbonyl. A suitable carbon based DMG containing thiocarbonyl is —(C=S)N-H—phenyl. Although compounds in which $X^h$ is S are suitable, compounds in which $X^h$ is O are preferred.

Although the foregoing method to produce benzocoumarins B1-1 or B1-2 is preferred herein, there are of course other appropriate methods. For example, the method of F. F. Abdel-Latif, *Gazz. Chim. Ital.*, 1991, 121, 9-10, to produce benzocoumarins may be modified by subsequent bromination or by bromine substitution on starting materials to obtain the benzocoumarin required herein. Methods cited in the review by G. Brigmann, et al., *Angew. Chem. Int. Ed. Eng.*, 1990, 29, 977-991, or the method of Jung, M. E., et al., *Tetrahedron Lett.*, 1988, 29, 2517-2520, or that of Deshpande, P.

P., et al., *Tetrahedron Lett.*, 1990, 31, 6313–6316 may also be employed.

FLOW SHEET A1

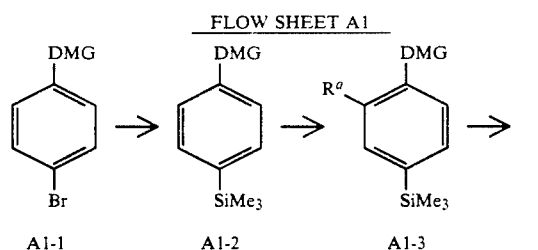

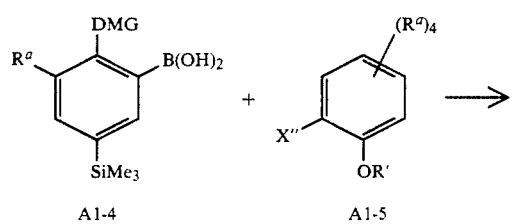

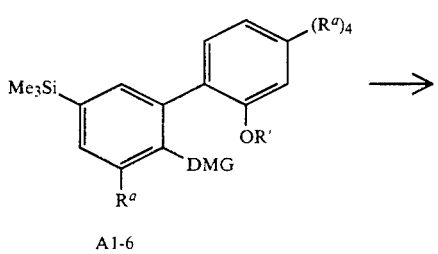

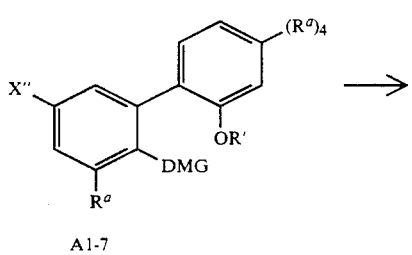

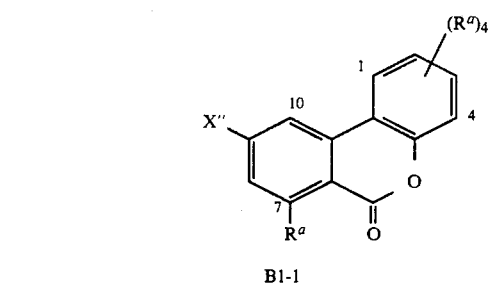

B1-1

FLOW SHEET A2

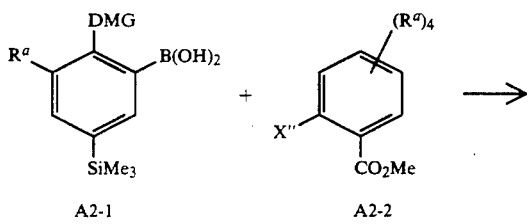

-continued
FLOW SHEET A2

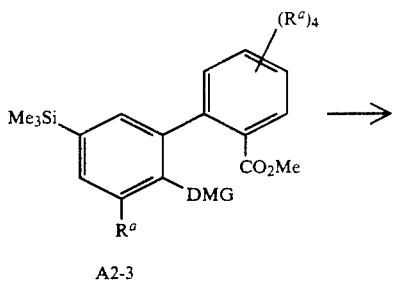

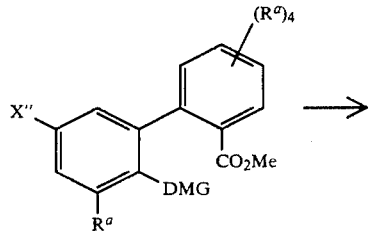

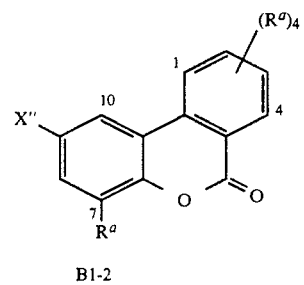

B1-2

The object compound of Flows Sheet A1 and A2, benzocoumarin B1-1 and B1-2, forms the nucleus of the 2-position substitution of the carbapenem compounds taught herein. As such it is shown to be $R^a$ substituted. However, it is immediately clear to those skilled in the art that certain $R^a$ listed above, if substituted on compounds A1-1, A1-5, A2-1 or A2-2 would not survive or permit the synthesis to compounds B1-1 or B1-2. Thus, where a certain $R^a$ is desired on compound B1-1 or B1-2 and this $R^a$ is not compatible with the synthesis scheme to produce, B1-1 or B1-2 then a compatible precursor substituent may be employed through the synthesis.

The identity of the precursor substituent employed is not crucial so long as it does not interfere with the synthesis to B1-1 or B1-2 and so long as it may be thereafter converted to a more desireable substituent. Preferred precursor substituents for $R^a$ are methyl, hydroxymethyl and protected hydroxymethyl.

Thus, as to the $R^a$ substituent on compound B1-1 or B1-2, it may be an $R^a$ with or without protecting groups stable to the conditions of producing compound B1-1 or B1-2, and stable to the conditions of subsequently adding B1-1 or B1-2, to the carbapenem. Alternatively, it may be a stable precursor substituent which is stable to the conditions of making B1-1 or B1-2, which is optionally stable to the conditions of adding B1-1 or B1-2, to the carbapenem and which is convertible to a desired $R^a$ or to another precursor substituent.

As stated above, the second stage synthesis is to attach the base benzocoumarin B1-1 or B1-2 to the 2-position of the carbapenem. One method to attach B1-1 or B1-2 to the base carbapenem utilizes the Grignard reaction. By this method however, B1-1 and B1-2 cannot be employed as such. Instead, the benzocoumarin precursor, i.e. the biphenyl, is employed as the Grignard reagent in the second stage synthesis. Thus, in this method, employing the Grignard reaction, the first stage synthesis, described above, is completed in the second stage synthesis. With stable $R^a$ or suitable precursor substituents therefor, biphenyl A1-7 may be added to azetidin-2-one B2 in a Grignard reaction as shown in Flow Sheet B. In a similar manner, biphenyl A2-4 may also be added where the methyl ester moiety has first been saponified to the acid. The Grignard reaction requires that A1-7, for example, be converted to a Grignard reagent by reaction with magnesium and 1,2-dibromoethane in THF from 20° C. to 60° C. and subsequently contacting A1-7 as a Grignard reagent with B2 in THF at from −70° C. to about 20° C. to produce azetidin-2-one B3. Alternatively, B1-1 may be reacted with t-butyl-lithium, n-butyllithium, or the like in THF at from −78° C. to −50° C. followed by the addition of magnesium bromide to produce the same Grignard reagent. $R^i$ of B3 is in practice pyrid-2-yl but may clearly be a variety of substituents including aromatic and heteroaromatic substituents. Further $R^i$ might be for example phenyl, 2-pyrimidinyl or 2-thiazolyl. Subsequently to this Grignard reaction, the biphenyl moiety is transformed to a benzocoumarinyl platform as previously described to produce B4.

Azetidin-2-one B4 is an intermediate that may be ring closed to a carbapenem. It is on this intermediate that $R^a$ or precursor substituents may be modified where such modification is incompatible with the carbapenem nucleus.

Compound B4 may be ring closed to carbapenem B5 by refluxing in xylene with a trace of p-hydroquinone for about 1 to 2 hours in an inert atmosphere. It is on this intermediate that final elaboration of $R^a$ from a precursor substituent, e.g. hydroxymethyl, may be accomplished. Removal of the carboxyl and hydroxyl protecting groups then provides the final compound of Formula I. Such final elaboration and deprotection is described in further detail below.

FLOW SHEET B

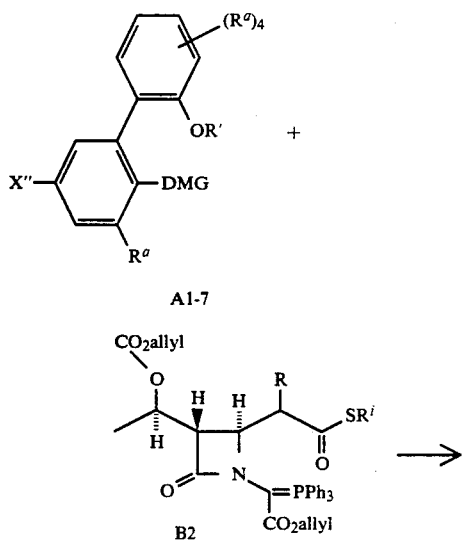

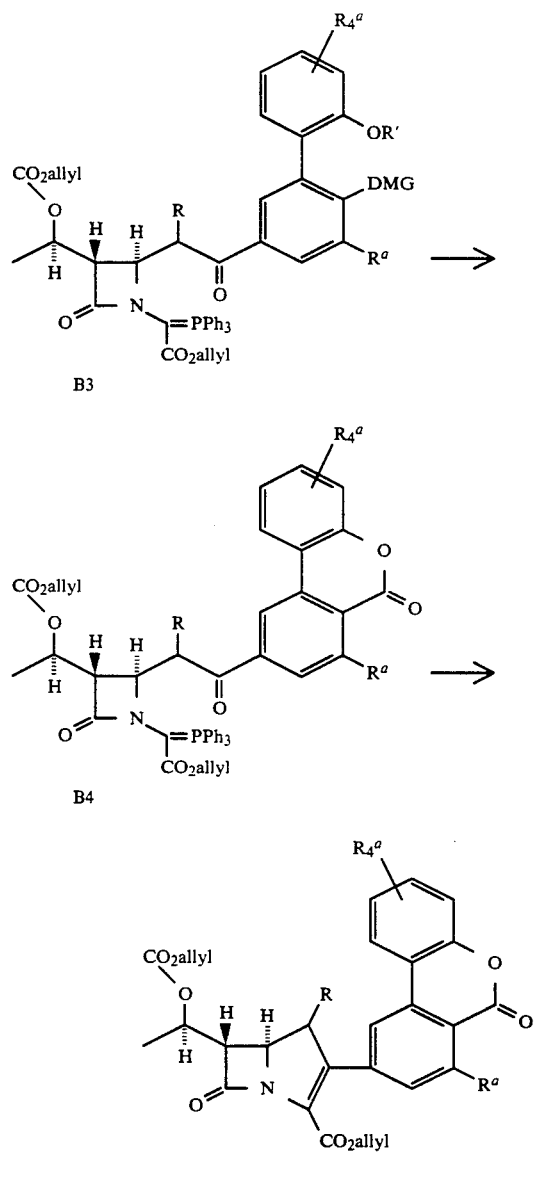

Flow Sheet C shows an alternative preferred second stage synthesis, i.e. attachment of the base benzocoumarin such as B1-1 to the 2-position of the carbapenem. This synthesis involves a palladium catalyzed cross-coupling reaction between a carbapenem triflate and a suitably substituted arylstannane, a process which is described in U.S. Pat. Appl. Ser. No. 650,011 filed Feb. 04, 1991, hereby incorporated by reference. In order to apply this synthesis, it is first necessary to modify benzocoumarin B1-1 to the trimethylstannylbenzocoumarin C3. This is accomplished by reacting benzocoumarin B1-1 with hexamethylditin in the presence of a palladium(0) catalyst such as tetrakis(triphenylphosphine)palladium(0) in an inert solvent such as toluene at from 25° to 110° C. for from 0.25-24 hours to provide the stannane C3. Referring to Flow Sheet C, the 2-oxocarbapenam C1 is reacted with a suitable trifluoromethanesulfonyl source, such as trifluoromethanesulfonic anhydride, in the presence of an organic nitrogen base, such as triethylamine, diisopropylamine and the like, in polar aprotic solvent, such as tetrahydrofuran or methylene chloride. Optionally, an organic nitrogen base, such as triethylamine and the like, is then added to the reaction solution followed immediately by a silylating agent, such as trimethylsilyl trifluoromethanesulfonate to provide intermediate C2. An aprotic polar coordinating solvent, such as DMF, 1-methyl-2-pyrrolidinone illustrated in Flow Sheet B. However, in certain cases it is advantageous for the $R^a$ substituent(s) of the stannane C3 to be introduced in a protected or precursory form. Final elaboration of $R^a$ from a precursor substituent, e.g. hydroxymethyl, may be accomplished on carbapenem intermediate C4. Removal of hydroxyl and carboxyl protecting groups then provides the final compound of Formula I. Such final elaboration and deprotection is described in further detail below.

FLOW SHEET C

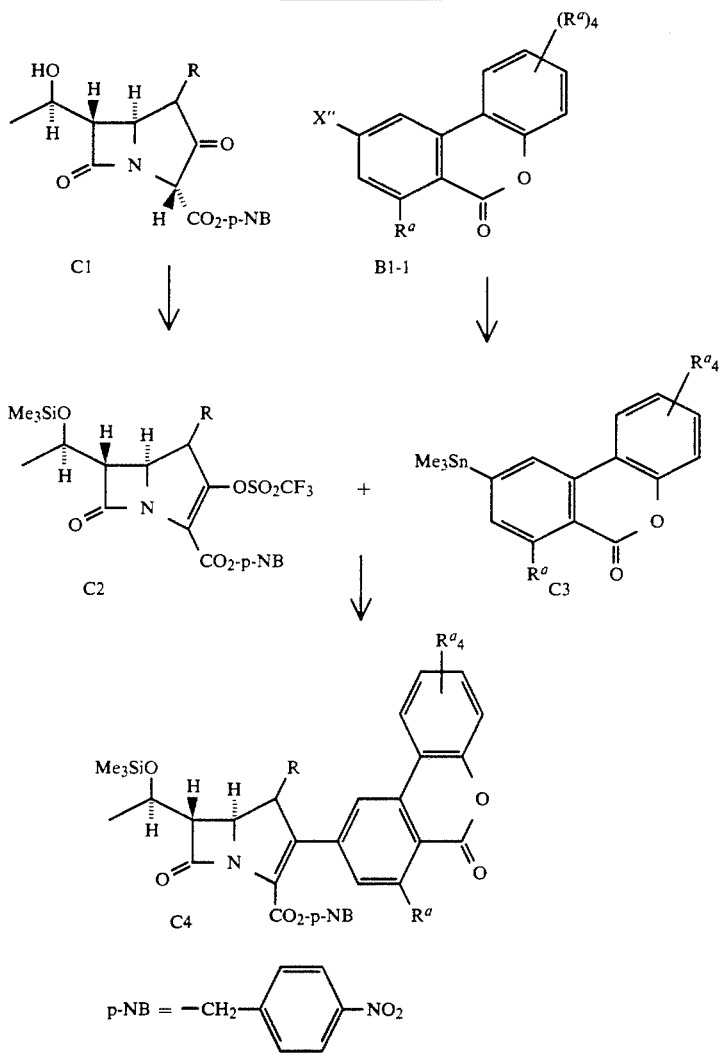

and the like, is optionally added. This is followed by the addition of a palladium compound, such as tris(dibenzylideneacetone)dipalladium-chloroform, palladium acetate and the like, optionally, a suitably substituted phenylphosphine, such as tris(4-methoxyphenyl)phosphine, tris(2,4,6-trimethoxyphenyl)phosphine and the like, and the stannane C3. A halide source, such as lithium chloride, zinc chloride or ammonium chlorides and the like, is added and the reaction solution is allowed to warm and is stirred at a suitable temperature, such as 0° to 50° C. for from a few minutes to 48 hours. The carbapenem C4 is obtained by conventional isolation/purification methodology known in the art.

Generally speaking, the milder conditions of the synthesis shown in Flow Sheet C allow for a wider range of functional groups $R^a$ to be present than the synthesis Azetidin-2-one B2, a pyridyl-thioester, is a well known compound in the production of carbapenems. Diverse synthetic schemes useful to make B2 may be imagined by the skilled artisan. Particularly useful to the instant invention is a synthetic scheme set out further in Flow Sheet D below in which the symbol R is as defined above. The steps for preparing intermediate B2 are analogous to the procedures described, for example, in U.S. Pat. Nos. 4,260,627 and 4,543,257; L. D. Cama et al. *Tetrahedron* 39, 2531 (1983); R. N. Guthikonda et al. *J. Med. Chem.*, 30, 871 (1987) hereby incorporated by reference.

FLOW SHEET D

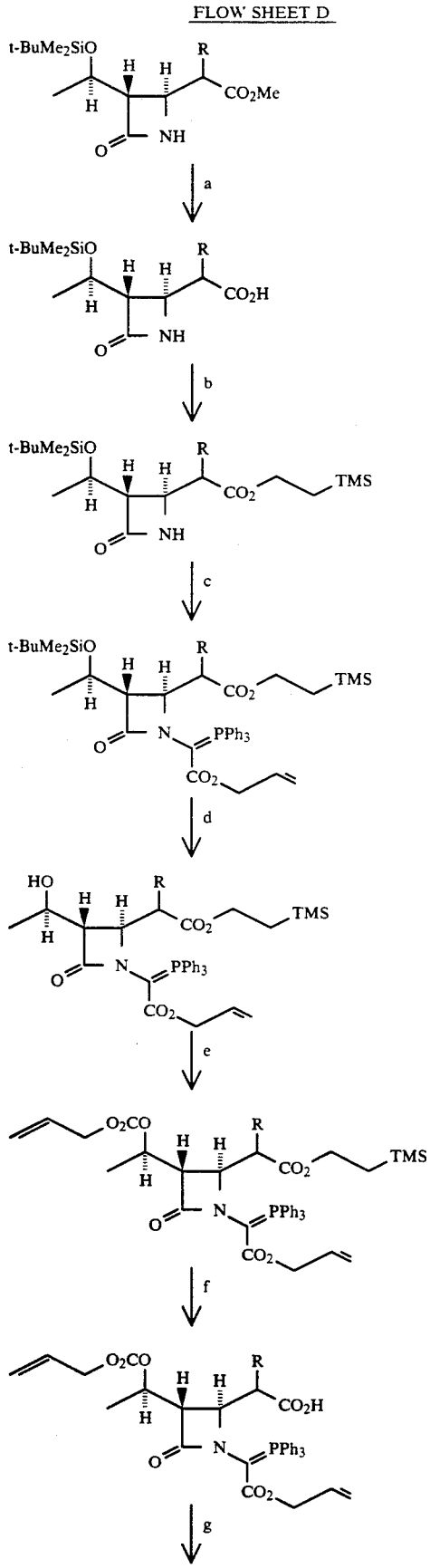

-continued
FLOW SHEET D

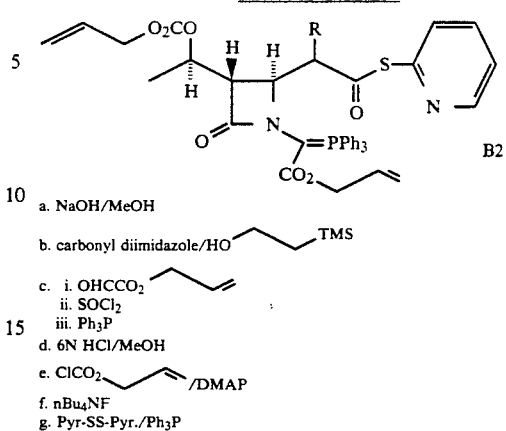

a. NaOH/MeOH
b. carbonyl diimidazole/HO~~~TMS
c. i. OHCCO₂~~~
   ii. SOCl₂
   iii. Ph₃P
d. 6N HCl/MeOH
e. ClCO₂~~~/DMAP
f. nBu₄NF
g. Pyr-SS-Pyr./Ph₃P The steps for preparing the 2-oxocarbapenam intermediate C1 are well known in the art and are explained in ample detail by D. G. Melillo et al., *Tetrahedron Lett.*, 1980, 21, 2783, T. Salzmann et al., *J. Am. Chem. Soc.*, 1980, 102, 6161, and L. M. Fuentes, I. Shinkai, and T. N. Salzmann, *J. Am. Chem. Soc.*, 1986, 108, 4675. The syntheses are also disclosed in U.S. Pat. No. 4,269,772, U.S. Pat. No. 4,350,631, U.S. Pat. No. 4,383,946 and U.S. Pat. No. 4,414,155 all assigned to Merck and Company, Inc. and hereby incorporated by reference.

The general synthesis description depicted above in the Flow Sheets shows a protected 1-hydroxyethyl substitution on the 6-position of the carbapenem. After final deprotection, a 1-hydroxyethyl substituent is obtained, which is preferred in most cases. However, it has been been found that with certain 2-side-chain selections, the ultimate balance of favorable properties in the overall molecule may be enhanced by selection of the 6-(1-fluoroethyl) moiety instead. Preparation of 6-fluoroalkyl compounds within the scope of the present invention is carried out in a straightforward manner using techniques well known in the art of preparing carbapenem antibacterial compounds. See, e.g., J. G. deVries et al., *Heterocycles*, 1985, 23, 1915; BE 900 718 A (Sandoz) and Japanese Patent Pub. No. 6-0163-882-A (Sanraku Ocean).

In the compounds of the present invention, one of the $R^a$ substituents must be of Type I. As a general matter, it is conjectured that anti-MRSA/MRCNS activity results from the configuration of the overall molecule uniquely conferred by the benzocoumarin nucleus. The Type I substituent provides still greater anti-MRSA/MRCNS activity to the molecule.

The Type II $R^a$ substituents are distinguishable from Type I substituents chemically and with respect to the biological properties which they confer. In related compounds, it has been found that the Type II substituted compounds afford greater water solubility and reduced potential for CNS side effects. Substituents which tend to confer improved water solubility on the overall compound have been found useful, since they are contemplated to thereby improve the transport of the compound involved. Although a substantial number and range of Type II substituents have been described herein, all of these are contemplated to be a part of the present invention based on the biological performance of substituents related in terms of their medicinal chemistry.

Since it is possible to combine, in the compounds of the present invention, the required Type I substituents with the optional Type II substituents, there can be obtained a combination of desired attributes in the final overall molecule not attainable with a single substituent, i.e., improved anti-MRSA/MRCNS activity together with enhanced water solubility.

Type I substituents employed in the compounds of the present invention may have quaternary nitrogen groups, and these include both cyclic and acyclic types, as is described under Type I. As already pointed out above, it is required that one, but no more than one, of the substituents $R^a$ must be a member selected from the group consisting of the definitions under Type I. It is optional that one, or at most three, of the remaining substituents may be a member selected from the group consisting of definitions under Type II. For example, $R^a$ at the 3-position may be Type I and $R^a$ at the 7-position may be of Type II, while the remaining substituents are hydrogen.

In preferred compounds of Formula I, $R^1$ is hydrogen. More preferably, $R^1$ is hydrogen and $R^2$ is (R)—CH$_3$CH(OH)— or (R)—CH$_3$CH(F)—. In the most preferred case, $R^1$ is hydrogen and $R^2$ is (R)—CH$_3$CH(OH)—. While R=H is usually preferred, there are instances in which R=CH$_3$ may provide improved chemical stability, water solubility, or pharmacokinetic behavior. The substituent R=CH$_3$ may be of either configuration, i.e., the $\alpha$ or $\beta$-stereoisomer. Additionally, in preferred compounds, at least $R^a$ in the 3-, 4- or 7-position of the benzocoumarin is other than hydrogen. In the most preferred compounds, in total, two $R^a$ substituents are other than hydrogen.

Preferred Type I. a) substituents include:

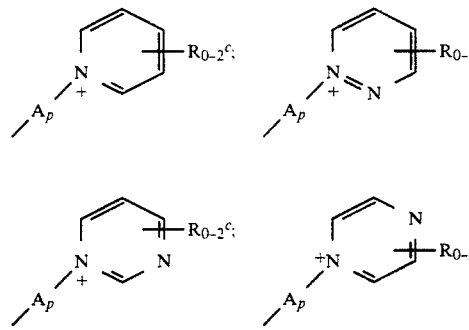

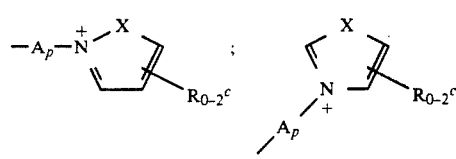

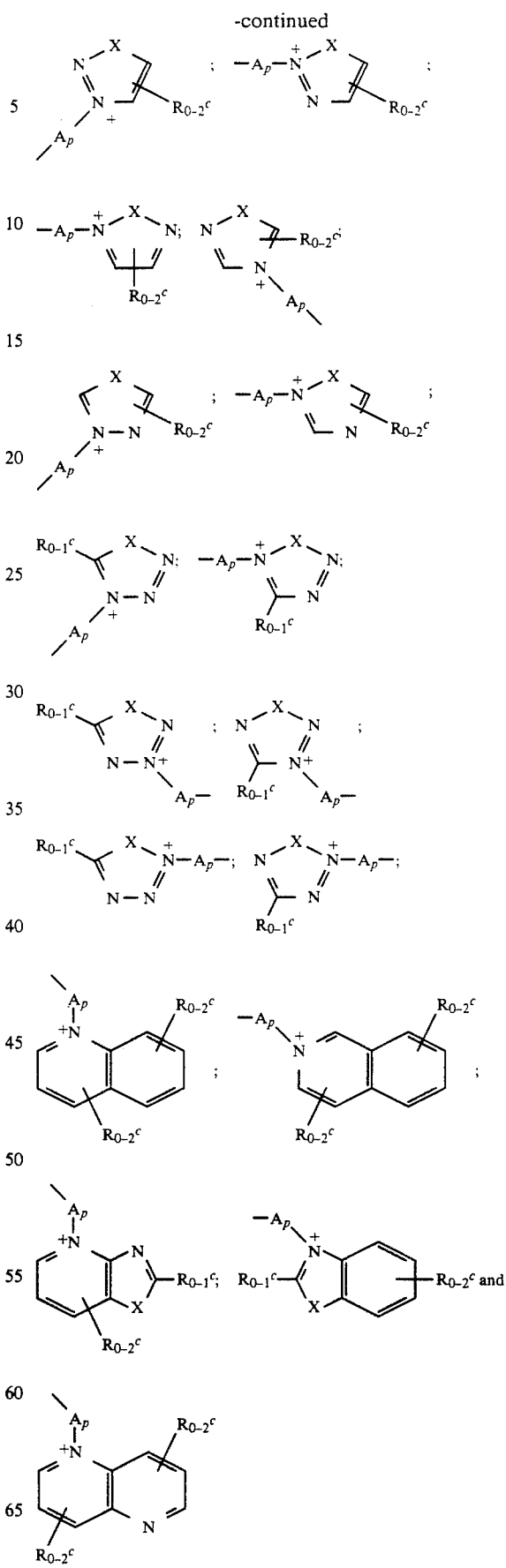

where X=O, S, or NR$^c$. For structures of Type I. a), where R$^c$ is shown to have an indefinite position, it may be attached to any carbon of the ring.

Preferred Type I. b) substituents include:

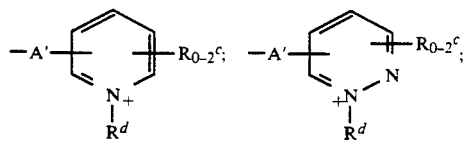
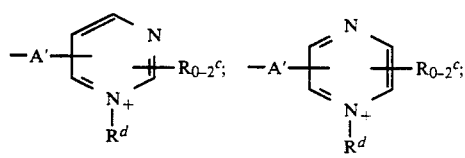
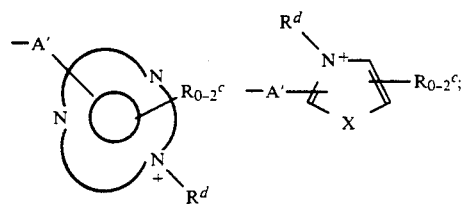

where the ring contains three carbon atoms;

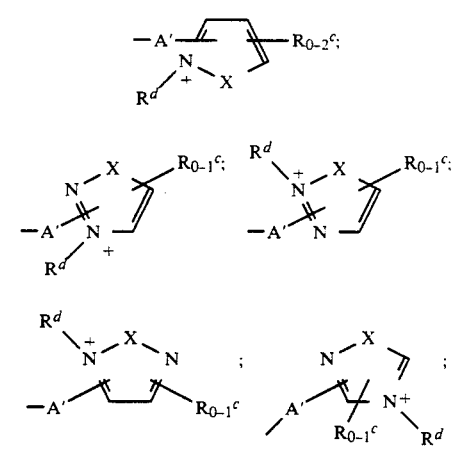
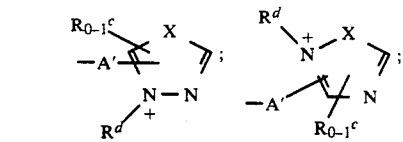
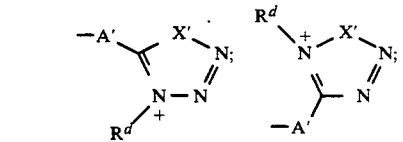
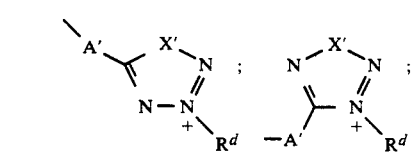
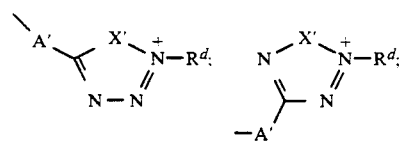
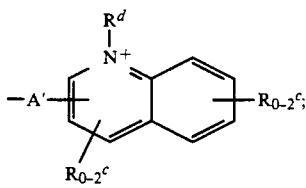
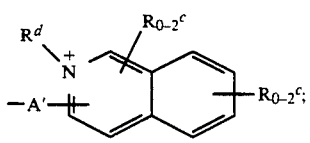
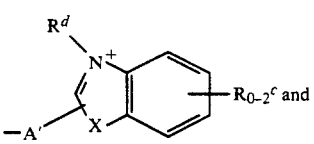
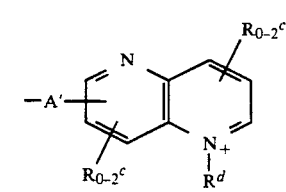

where X=O, S, or NR$^c$ and X'=O or S. For structures of Type I. b), where R$^c$ and/or A' are shown to have indefinite positions, they are independently attached to any carbon atom of the ring.

Preferred Type I. c) substituents include:

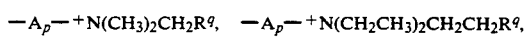
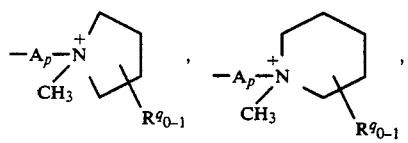
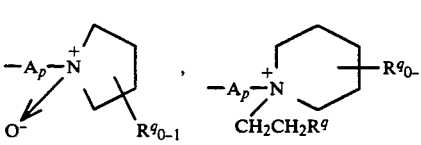
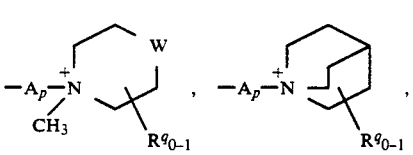

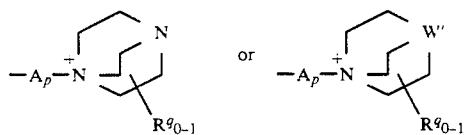

where W is O, S, NR$^e$, N(O)R$^e$, SO, SO$_2$ or N$^+$(R$^e$)$_2$ and W' is N$^+$R$^e$ or NO. For structures of Type I. c), where R$^q$ is shown to have an indefinite position, it may be attached to any carbon atom of the ring.

Preferred Type I. d) substituents include:

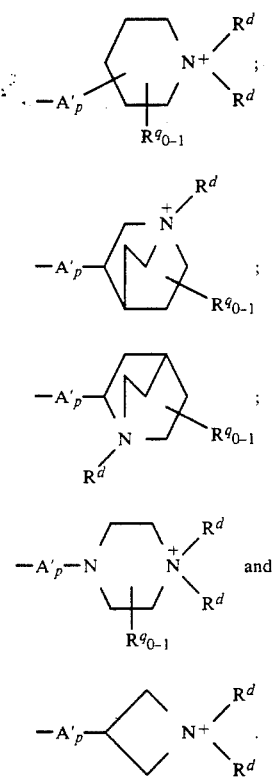

For structures of Type I. d), where R$^q$ and/or A'$_p$ is shown to have an indefinite position, it may be attached to any carbon atom of the ring.

The R$^c$ substituents herein are intended to represent suitable further substituents on the Type I. a) or b) substituents for the benzocoumarinyl ring. As seen above, these Type I. a) or b) substituents are monocyclic or bicyclic aromatic groups containing heteroatoms. Given this class of primary substituent, further suitable substituents may be readily discovered in the penem and carbapenem art. For example, suitable substituents for Type I. a) or b) substituents are generally taught in U.S. Pat. No. 4,729,993 assigned to Merck and Co. or in U.S. Pat. No. 4,746,736 assigned to Bristol-Myers Co. These patents are hereby incorporated by reference.

Broadly, R$^c$ may be the same or different and may be selected on an independent basis from the group as defined above. While a single such substitution is preferred, there is occasion to use up to two such substituents on an R$^a$, e.g., where it is desired to enhance the effect of a particular substituent group by employing multiple substituents. The particular choice of R$^c$ will depend upon the situation. For instance, a specific R$^c$ may lend particular stability to a nitrogen cation. At other times it may be desired to employ a substituent known to enhance antibacterial activity of the overall molecule against a particular bacterium, for example, while also employing a substituent known to improve some other property such as water solubility or the duration of action of the overall molecule.

The scope of R$^c$ herein includes two specific Types of further substituent attached to the Type I. a) or b) substituent. A first Type of R$^c$ are those attached to a ring carbon and a second Type of R$^c$ are those attached to a neutral ring nitrogen. Persons skilled in the art will readily recognize that a wide range of organic substituents are suitably used as R$^c$. Persons skilled in the art will also recognize that some substituents including the —NR$^y$R$^z$ substituents, useful for one purpose of R$^c$, i.e. carbon substitution, are not equally useful in the other, i.e. nitrogen substitution.

Preferred R$^c$ attached to ring carbon atoms are —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where M$^b$ is defined above. Preferred R$^c$ attached to neutral ring nitrogen atoms are —H, —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, —CH$_2$CH$_3$, —CH$_2$CONH$_2$ and —CH$_2$CON(C$_1$-C$_4$alkyl) where M$^b$ is defined above.

It is preferred that each Type I. a) or b) substituent have no more than two R$^c$ substituents which are other than hydrogen. Thus, the formula shown above for Type I. a) substituents has up to two R$^c$ substituents with the remainder of course being hydrogen. Further, the formula for the Type I. b) substituent also allows up to two R$^c$. In accordance with these formulae, the previously listed more specific structures should be interpreted to have no more than two R$^c$ for each monocyclic or bicyclic group. Similarly for Type I. c) or d) substituents it is preferred that any monocylic or bicyclic group have no more than a single R$^q$ substituent.

The scope of R$^d$ includes a single type of further substituent attached a Type I. b) or d) substituent. The R$^d$ substituents are attached to a cationic nitrogen which may or may not be aromatic. Preferred R$^d$ attached to cationic nitrogen atoms are hydrogen, —CH$_3$, CH$_2$CH$_3$, —CH$_2$CH$_2$CH$_3$, —CH$_2$COOM$^b$, —CH$_2$SO$_3$M$^b$, —NH$_2$ and 0$^{(-)}$, where M$^b$ is defined above.

The formulas depicting Type Ia, Ib, Ic, and Id substituents show positively charged states for those substituents. It is understood that certain of those substituents, which are cationic by virtue of having a protonating hydrogen atom attached to a nitrogen atom, may also exist or be produced under certain conditions as a neutral substituent by virtue of the absence of such a hydrogen atom (ie. in Type Ib, when there is no R$^d$; in Type Ic, when there is no R$^w$; and in Type Id, when there is zero to one R$^d$, depending on Type of heterocycle). Whether such a Type Ia, Ib, Ic, or Id substituent will be predominately cationic or neutral in a given physical state will be governed by principles of acid-base chemistry, which are well known to those skilled in the art. For example, the particular ratio of neutral form to cationic form will depend upon the basicity of the amine and acidity of a solution. When such a substituent is in a protonated quaternized state, the compound exists as a zwitterion which is internally balanced as to charge or as an ammonium salt which is externally balanced. In illustration, if there is no $R^d$ on a Type Ib substituent, it is understood that such a substituent is neutral (there is no positive charge on the nitrogen). A compound containing such a substituent is typically produced in this form as a salt, wherein M is an alkali metal, and may exist in solution in its neutral form. However, depending upon conditions, a compound containing a neutral Type Ib substituent may be in equilibrium with, and may also be represented by a formula showing, the corresponding compound containing the quaternized protonated substituent where $R^d$ is present and is a hydrogen atom. Furthermore the same compound may exist with the Type Ib substituent in a completely protonated quaternized form, for instance in an aqueous solution in the presence of a stoichiometric amount of a strong mineral acid. It is intended herein that both the protonated (cationic) and the unprotonated (neutral) forms of Type Ia, Ib, Ic and Id substituents of the type just described are within the scope of the present invention.

Suitable A spacer moieties include $-CH_2-$, $-CH_2CH_2-$, $-CH_2CH_2CH_2-$, $-CH_2CH_2CH_2CH_2-$, $-OCH_2CH_2-$, $-SOCH_2-$, $-SO_2CH_2-$, $-SCH_2CH_2-$, $-SOCH_2CH_2-$, $-SO_2CH_2CH_2-$, $-NHCH_2CH_2-$, $-N(CH_3)CH_2CH_2-$, $-CH_2N(CH_3)CH_2CH_2-$, $-CONHCH_2CH_2-$, $-SO_2NHCH_2CH_2-$, $-COCH_2-$, $-CH=CHCH_2-$ and $-CH_2OCH_2CH_2-$. Preferably, where Q is O, S, NH or $N(C_{1-4}alkyl)$, then n is 2–6.

Suitable A' are listed for A above. Further A' may suitably be $-O-$, $-S-$, $-NH-$, $-SO_2-$, $-SO_2NH-$, $-CONH-$, $-CH=CH-$, $-CH_2S-$, $-CH_2NH-$, $-CONHCH_2-$ or $-SO_2NHCH_2-$.

The Type I. cationic substituents are generally added to the benzocoumarin following attachment of the benzocoumarin to the carbapenem. Conveniently, the benzocoumarin side-chain should be synthesized with a precursor substituent which may be elaborated into the desired cationic substituent. The identity of the precursor substituent will vary according to the particular $R^a$ desired. For example, one such precursor substituent is $-A-OH$, such as hydroxymethyl.

The hydroxymethyl precursor substituent may be elaborated into cationic substituents of Type I.a) by converting the hydroxyl into an active leaving group such as an iodide (giving $-A-I$) followed by reaction with a desired nitrogen containing aromatic compound. More particularly, two alternative procedures may be utilized to produce a leaving group on the moiety $-A-$ and subsequently to replace such a leaving group with cationic substituents of the type just described.

For a first procedure, the hydroxyl group of $-A-OH$ may be converted to a methanesulfonate group by treating with methanesulfonyl chloride in the presence of triethylamine. A suitable solvent, e.g., dichloromethane, is employed and the reaction is carried out at reduced temperatures. In turn, the methanesulfonate intermediate which itself is a good leaving group may be converted to the reactive iodide derivative by treatment with sodium iodide in a suitable solvent, e.g., acetone, at reduced or ambient temperatures. Alternatively, the hydroxyl group may be directly converted into the iodide group by common methods known to the art. For example, treatment of the hydroxyl group with methyl triphenoxyphosphonium iodide in a suitable solvent, such as dimethylformamide, at reduced or ambient temperatures, directly provides the desired iodide. Once the iodide has been formed, the introduction of the cationic substituent is accomplished simply by treating the iodide with the desired nitrogen containing compound, e.g. a heteroaromatic compound such as pyridine. The reaction will proceed in a suitable solvent, such as acetonitrile, at or about room temperature. This displacement reaction may also be facilitated by the addition of excess silver trifluoromethanesulfonate to the reaction mixture, in which case reduced temperatures are often desirable.

For a second procedure, the hydroxyl group of $-A-OH$ may be converted into the reactive trifluoromethanesulfonate (triflate) group. However, such an activating group cannot be isolated by conventional techniques but may be formed and used in situ. Thus, treatment of the hydroxyl group with trifluoromethanesulfonic (triflic) anhydride in the presence of a hindered, non-nucleophilic base such as 2,6-lutidine, 2,4,6-collidine, or 2,6-di-tert-butyl-4-methylpyridine in a suitable solvent, such as dichloromethane, at reduced temperatures provides for the generation of the triflate activating group. Introduction of the cationic group is then accomplished by reacting the above triflate in situ with the desired nitrogen containing compound at reduced temperature. In certain cases it is possible and desirable to use the reacting nitrogen containing compound as the base for the formation of the triflate activating group. In this case treatment of the hydroxyl group with triflic anhydride in the presence of at least two equivalents of the reacting nitrogen compound under the conditions described above provides the cationic substituent.

The above are representative of suitable leaving groups: alkylsulfonyloxy, substituted alkylsulfonyloxy, arylsulfonyloxy, substituted arylsulfonyloxy, fluorosulfonyloxy and halogen. The common sulfonate leaving groups are: methanesulfonyloxy, trifluoromethanesulfonyloxy, fluorosulfonyloxy, p-toluenesulfonyloxy, 2,4,6-tri-isopropylbenzenesulfonyloxy, p-bromo-benzenesulfonyloxy and p-nitrobenzenesulfonyloxy. The preferred halo leaving groups are bromo and iodo. These alkyl and arylsulfonate leaving groups may be prepared using an analogous route to the one described above using the sulfonyl chloride or the sulfonic anhydride.

Where the cationic substitution has a substituent $R^c$, the most facile method of providing such a substituent is to employ as the reactant in the preparation methods described above a nitrogen containing compound which already has the desired substituent. Such substituted compounds are readily available starting materials or may be prepared in a straight-forward manner using known literature methods.

The Type I.b) cationic substituents are prepared by quaternization of an aromatic ring nitrogen of a neutral precursor substituent on the benzocoumarin ring. Examples of neutral precursor substituents are $-CONHCH_2-$(2-pyridyl), $-CONHCH_2-$(4-pyridyl) or $-SO_2CH_2-$(4-pyridyl). Quaternization is accomplished by reacting the nitrogen compound in an inert organic solvent (e.g. $CH_2Cl_2$) at about 0° C. to room temperature with an alkylating agent $R^d-Y$ where $R^d$ is given above and Y is a leaving group such as iodide, bromide, mesylate (methanesulfonate), tosylate (p-toluenesulfonate) or O-triflate. Alternatively, the aromatic ring nitrogen may be quaternized by reaction with an oxidizing agent such as 3-chloroperbenzoic acid (giving the N-oxide) or an amidinating reagent such as o-(2,4,6-triisopropylbenzenesulfonyl)hydroxylamine (giving the N-amino derivative) in a suitable solvent (e.g. dichloromethane or $CH_3CN$) at about room temperature. In addition, the neutral precursor substituent may be rendered cationic through protonation of the basic aromatic ring nitrogen. This may be accomplished by treatment of the neutral precursor with a suitable inorganic or organic acid, e.g. hydrochloric acid, phosphoric acid, hydrobromic acid, acetic acid or benzoic acid. Protonation may further be accomplished by a carboxylic acid function elsewhere in the molecule, including the C-3 carboxyl on the carbapenem. The neutral precursor substituent may be already attached to the benzocoumarin ring at the time of its connection to the carbapenem, or it may be elaborated from a simpler precursor after connection to the carbapenem. An example of a precursor substituent for elaboration is —A'—OH such as hydroxymethyl. In one suggested synthesis, the hydroxyl may be converted to a reactive leaving group such as iodo as described above. The iodide is then reacted in a nucleophilic displacement reaction with a nitrogen containing aromatic compound which has a nucleophilic side-chain substituent such as $CH_2SH$ or $CH_2NH_2$. In this displacement reaction, it is the side-chain substituent that is the reacting nucleophile and not the aromatic ring nitrogen. Suitable substrates for this reaction include 2-(mercaptomethyl)-pyridine, 2-aminopyridine, 2-(aminomethyl)pyridine or 4-(mercaptomethyl)pyridine. The reaction is carried-out in an inert organic solvent, e.g. methylene chloride, at from about 0° C. to room temperature in the presence of a non-nucleophilic base such as triethylamine or diisopropylethylamine. Quaternization or protonation of the aromatic ring nitrogen as described above then gives the Type I.b) cationic substituent. A second suggested synthesis of a Type I.b) cationic substituent starting from a precursor —A'—OH (e.g. hydroxymethyl) consists of oxidation of the alcohol functionallity to an aldehyde followed by Wittig-type olefination with an appropriate nitrogen-containing aromatic substituted reagent, and finally quaternization. The oxidation may be conveniently accomplished by a Swern oxidation employing oxalyl chloride-dimethylsulfoxide followed by triethylamine. The reaction is conducted in methylene chloride as a solvent at from $-70°$ C. to 0° C. The Wittig reaction is carried-out by reacting the aldehyde with the desired Wittig reagent in a polar solvent such as acetonitrile or dimethylsulfoxide at about room temperature. Suitable Wittig reagents include: pyridylmethylene-triphenylphosphorane, quinolylmethylene-triphenylphosphorane, and thiazolylmethylenetriphenylphosphorane. Quaternization or protonation as described above then completes the synthesis of the Type I.b) cationic substituent. Depending on the particular $R^a$ of Type I.b) that is desired, many other synthesis schemes may be employed, as would be apparent to an organic chemist skilled in the art.

The Type I.c) cationic substituents may be prepared in an analogous manner to that described for I.a) substituents except that the nitrogen containing compound employed in the displacement reaction is an aliphatic amine (i.e. $NR^yR^zR^w$). However, in cases where the amino group is directly bonded to the benzocoumarin nucleus (i.e. $-A_pN+R^yR^zR^w$ where p=0) the amine is most conveniently attached to the benzocoumarin prior to its incorporation into the carbapenem system. If such an amine is primary or secondary, it may require protection with a suitable amine protecting group during the steps employed to attach the benzocoumarin to the carbapenem. Tertiary amines require no protection and may be quaternized or protonated as described for the Type I.b) cationic substituents.

The Type I.d) cationic substituents are prepared by quaternization or protonation of a non-aromatic ring nitrogen of an appropriate neutral precursor substituent on the benzocoumarin ring. Quaternization or protonation is accomplished as described above for the Type I.b) substituents. As with the Type I.b) substituents, the neutral precursor may already be attached to the benzocoumarin ring at the time of its connection to the carbapenem, or the neutral precursor may be elaborated from a simpler precursor substituent on the benzocoumarin ring after its connection to the carbapenem. Examples of neutral precursor substituents are: —CONH(3-quinuclidinyl), —CONH[4-(N-methylpiperidinyl)], —$SO_2CH_2CH_2$[2-(N-methylpyrrolidinyl)], —$SO_2NH$[1-(4-methylpiperazinyl)] and —$CH_2$[1-(4-methylpiperazinyl)]. Elaboration of the neutral precursor substituent from a simpler substituent such as hydroxymethyl may be accomplished in an analogous manner to that described previously for the Type I.b) substituents by employing appropriate reagents to introduce the Type I.d) non-aromatic ring nitrogen moiety which is subsequently to be quaternized or protonated.

It should be clear that for any of the Type I.a) to I.d) substituents, that the substituent may be suitably formed on the benzocoumarin prior to addition to the carbapenem. Thus, the substituent may be formed on C3 and reacted with C2 to form the protected carbapenem C4. For example, 3-hydroxymethyl-9-trimethylstannyl-benzocoumarin, i.e. C3, may be substituted by reaction with triflic anhydride and N-methylimidazole in a suitable solvent, such as, dichloromethane under nitrogen at $-78°$ C. to room temperature to form a Type I.a) substituted benzocoumarin, i.e. C3. This substituted benzocoumarin may be reacted with C2 employing conditions otherwise described herein and specifically using an ammonium chloride source.

Suitable $R^a$ are described above in the text associated with Formula I. Among preferred $R^a$ of Type II are $C_{1-4}$ alkyl mono-substituted with hydroxy, such as, hydroxymethyl; formyl; alkoxycarbonyl, such as, —$COOCH_3$; carbamoyl, such as, —$CONH_2$; hydroximinomethyl, such as, —CH=NOH; or cyano.

In regard to this preferred substitution, a hydroxymethyl may be obtained in any of positions 7, 1, 2, 3 or 4 for $R^a$ as follows. As one method, hydroxymethyl may be substituted on any of rings A1-4 and A1-5 or A2-1 and A2-2 by standard procedures and appropriately protected. Alternatively, methyl, as a precursor substituent, is substituted on starting materials A1-4 and A1-5 or A2-1 and A2-2 in the appropriate positions by well known means and the starting materials reacted to a corresponding methyl-substituted B1-1 or B1-2 according to Flow Sheet A1 or A2 respectively. Subsequently, the methyl substituent(s) of methyl substituted B1-1 or B1-2 may be oxidized to bromomethyl with N-bromosuccinimide. This oxidation of the precursor substituent, methyl, is advantageously performed prior to substituting the benzocoumarin on the azetidin-2-one as the oxidizing conditions are incompatible with either the azetidin-2-one or the subsequent carbapenem. In the case of the bromomethyl substituent, conversion to an hydroxymethyl substituted B1-1 or B1-2 may be accomplished by a three-step sequence. Reaction of the bromomethyl compound with potassium acetate in DMF at 80° C. gives the corresponding acetoxymethyl compound. Removal of the acetate group, e.g. by hydrolysis with methanolic sodium hydroxide or by reduction with diisobutylaluminium hydride in THF, gives the hydroxymethyl substituted compound B1-1 or B1-2. Further elaboration of hydroxymethyl substituted A1-7 or A2-4 according to Flow Sheet B produces a corresponding B4 and B5.

The preferred formyl substitution on the benzocoumarin may be obtained on B5 from the hydroxymethyl substitution, in the case of $R^a$, by a Swern oxidation. For example, B5 is oxidized in methylene chloride at from $-70°$ C. to room temperature employing oxalyl chloride-dimethyl sulfoxide followed by triethylamine as the active agent. Obviously, the position of the resultant formyl substitution will depend upon the position of the hydroxymethyl substitution on B5.

The preferred —CH=NOH substitution on the benzocoumarin may be conveniently obtained from the formyl substitution just described. This is accomplished simply by exposing the formyl substituted compound to hydroxylamine in an appropriate solvent at room temperature.

The preferred cyano substitution on the benzocoumarin may be obtained from the —CH=NOH substitution just described. The —CH=NOH substituted compound is dehydrated with triflic anhydride and triethylamine in a solvent at $-70°$ C.

The —COOCH$_3$ substitution on the benzocoumarin may be obtained from the hydroxymethyl substituted B4 described above. For example, compound B4 is oxidized with Jones reagent to convert the hydroxymethyl substituent to the carboxylic acid group. The oxidation with Jones reagent may be incompatible with the carbapenem and thus is optimally performed before ring closure. Prior to ring closure, the carboxylic acid group is esterified by sequentially contacting with 1-ethyl-3-(3-dimethyl-aminopropyl)carbodiimide hydrochloride, 1-hydroxybenzotriazole, and methanol in an organic solvent at room temperature. Substituted esters may of course be obtained by replacing methanol with the corresponding substituted alcohol. Alternatively, a methyl substituted B1-1 or B1-2, as described above, may be oxidized with chromium trioxide or $^nBu_4NMnO_4$ to form carboxy.

The preferred carbamoyl substitution on the benzocoumarin, may be obtained from B3 or B4 by oxidizing the hydroxymethyl group with Jones reagent to the corresponding carboxylic acid group as described above. This carboxylic acid substituent is converted to the carboxamide group, —CONH$_2$, by sequentially contacting with 1-ethyl-3-(3-dimethylaminopropyl)carbodiimide hydrochloride, 1-hydroxybenzotriazole, and ammonia in an organic solvent at room temperature. Substituted amides may of course be obtained by replacing ammonia with the corresponding substituted amine. In contrast to the carboxyl substitution, this carbamoyl group requires no protection for the conditions of carbapenem cyclization.

Compounds substituted with the preferred $R^a$ of Type II just described may also be obtained by employing the synthesis shown in Flow Sheet C. In this case, the synthetic transformation just described may be carried-out on intermediate B1-1 or C3 prior to attachement of the benzocoumarin side chain to the carbapenem or on C4 after such attachment.

In addition to or including the above, suitable $R^a$ of Type II include:

| | |
|---|---|
| —OCH$_3$ | —OCH$_2$CO$_2$CH$_3$ |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$CH$_3$ | —CH=NOCMe$_2$CO$_2$CH$_3$ |
| —CH=NOCMe$_2$CONH$_2$ | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$CH$_3$ |
| —CONHOH | —CONHOCH$_3$ |
| —tetrazolyl | —CO$_2$CH$_3$ |
| —SCF$_3$ | —CONHSO$_2$Ph |
| —CONHSO$_2$NH$_2$ | —SO$_2$CF$_3$ |
| —SO$_2$NHCN | —SO$_2$NHCONH$_2$ |
| —CH=CHCN | —CH=CHCONH$_2$ |
| —CH=CHCO$_2$CH$_3$ | —C≡C—CONH$_2$ |
| —C≡C—CN | —CH$_2$OH |
| —CH$_2$N$_3$ | —CH$_2$CO$_2$CH$_3$ |
| —SO$_2$CH$_2$CH$_2$OH | —SCH$_2$CONH$_2$ and |
| —CH$_2$I. | |

In the preparation methods described above, the carboxyl group at the 3-position and the hydroxyl group at the 8-position of the carbapenem remain blocked by protecting groups until the penultimate product is prepared. Suitable hydroxyl protecting groups, P', are silyl groups such as trialkylsilyl, aryl(alkyl)alkoxysilyl, alkloxydiarylsilyl and diarylalkylsilyl and carbonate groups such as alkyloxy and substituted alkyloxycarbonyl, benzyloxycarbonyl, substituted benzyloxycarbonyl, allyloxycarbonyl and substituted allyloxycarbonyl. The preferred protecting groups, in addition to or including those shown in the schemes, are t-butylmethoxyphenylsilyl, t-butoxydiphenylsilyl, trimethylsilyl, triethylsilyl, t-butyldimethylsilyl, o-nitrobenzyloxycarbonyl, p-nitrobenzyloxycarbonyl, benzyloxycarbonyl, t-butyloxycarbonyl, 2,2,2-trichloroethyloxycarbonyl and allyloxycarbonyl. Suitable carboxyl protecting groups M, in addition to or including those shown in the schemes are described herein below.

Deblocking may be carried out in a conventional manner. For compounds prepared according to Flow Sheet B, deprotection may be carried out in a palladium catalyzed reaction in a solution containing potassium 2-ethylhexanoate and 2-ethylhexanoic acid or, alternatively, another suitable nucleophile such as pyrrolidine. Alternatively, for those prepared via Flow Sheet C, deprotection is conducted sequentially. Thus, compound C4 is exposed initially to aqueous acidic conditions, acetic acid or dilute HCl or the like, in an organic solvent such as tetrahydrofuran containing some H$_2$O at 0° C. to ambient temperature for from a few minutes to several hours. The resulting desilylated carbapenem may be isolated by conventional techniques, but is more conveniently taken into the final deprotection process. Thus, addition of an inorganic base such as NaHCO$_3$ or KHCO$_3$ and a catalyst such as 10% Pd/C or 5% Al$_2$O$_3$ followed by hydrogenation provides for the removal of the p-nitrobenzyl protecting group and the formation of the final compound of Formula I.

The overall molecule must be electronically balanced. Since a quaternary nitrogen is present in the compounds of the present invention, a balancing anion must also, in that case, be present. This is usually accomplished by allowing COOM to be COO⁻. However, where M is, e.g., a pharmaceutically acceptable ester, a counterion (anion) Z⁻ must be provided, or alternatively, an anionic substituent might be utilized. A counterion must also be provided or additional anionic substituent utilized where there is more than one quaternary nitrogen. Further, it is within the scope of this invention to utilize an anionic substituent where the quaternary nitrogen is already balanced by COOM=COO⁻. In that case, it will be understood that it is necessary to provide a counterion (cation) for the anionic substituent. However, it is well within the skill of a medicinal chemist, to whom there is available many suitable anionic and cationic counterions, to make such choices.

With reference to the above definitions, "alkyl" means a straight or branched chain aliphatic hydrocarbon radical.

The term "quaternary nitrogen" as used herein refers to a tetravalent cationic nitrogen atom including the cationic nitrogen atom in a tetra-alkylammonium group (e.g. tetramethylammonium, N-methylpyridinium), the cationic nitrogen atom in a protonated ammonium species (e.g. trimethylhydroammonium, N-hydropyridinium), the cationic nitrogen atom in an amine N-oxide (e.g. N-methylmorpholine-N-oxide, pyridine-N-oxide), and the cationic nitrogen atom in an N-amino-ammonium group (e.g. N-aminopyridinium).

The term "heteroatom" means N, S, or O, selected on an independent basis.

The term "heteroaryl" has been defined herein, in relation to the $R^x$ group, to have a specific and limited meaning, being only monocyclic. While the cationic groups I. a) and b) also clearly include heteroaryl groups, being both monocyclic and bicyclic, the term "heteroaryl" has not been used in association with the definitions of those cationic groups above. It is required that the monocyclic heteroaryl have at least one nitrogen atom, and optionally at most only one additional oxygen or sulfur heteroatom may be present. Heteroaryls of this type are pyrrole and pyridine (1 N); and oxazole, thiazole or oxazine (1 N+1 O or 1 S). While additional nitrogen atoms may be present together with the first nitrogen and oxygen or sulfur, giving, e.g., a thiadiazole (2N's+1S), the preferred heteroaryls are those where *only* nitrogen heteroatoms are present when there is more than one. Typical of these are pyrazole, imidazole, pyrimidine and pyrazine (2 N's) and triazine (3 N's).

The heteroaryl group of $R^x$ is always optionally mono-substituted by $R^q$, defined above, and substitution can be on one of the carbon atoms or one of the heteroatoms, although in the latter case certain substitutent choices may not be appropriate.

Listed in Table I are specific compounds of the instant invention:

TABLE I

Structure: where R" is F or OH, R is H or Me and E is one of two bicyclic structures with $(R^a)_4$ substitution and $R^a$ at position 7.

| M | $R^a$ | Position |
|---|-------|----------|
| (−) | −CH₂N⁺(pyridyl)−NH₂ | 7 |
| (−) | −CH₂N⁺(pyridyl)−NH₂ | 3 |
| (−) | −CH₂N⁺(pyridyl)−NH₂ | 4 |
| (−) | −CH₂N⁺(pyridyl)−NH₂ | 2 |
| (−) | −CH₂N⁺(pyridyl)-NH₂ | 3 |
| (−) | −CH₂N⁺(pyridyl)-NH₂ | 7 |
| (−) | −CH₂N⁺(pyridyl)-NH₂ | 3 |
| (−) | −CH₂N⁺(pyridyl)-NH₂ | 4 |

TABLE I-continued

| | | |
|---|---|---|
| (−) | —CH$_2$N$^+$ ⟨pyridine⟩-NH$_2$ | 2 |
| (−) | —CH$_2$N$^+$ ⟨pyridine⟩-NH$_2$ | 1 |
| (−) | —CH$_2$N$^+$ ⟨imidazole⟩-N-CH$_3$ | 7 |
| (−) | —CH$_2$N$^+$ ⟨imidazole⟩-N-CH$_3$ | 3 |
| (−) | —CH$_2$N$^+$ ⟨imidazole⟩-N-CH$_3$ | 4 |
| (−) | —CH$_2$N$^+$ ⟨imidazole⟩-N-CH$_3$ | 2 |
| (−) | —CH$_2$N$^+$ ⟨triazole⟩-N-CH$_3$ | 3 |
| (−) | —N$^+$ ⟨imidazole⟩-N-CH$_3$ | 7 |
| (−) | —N$^+$ ⟨pyridinium⟩ | 7 |
| (−) | —CH$_2$N$^+$ ⟨triazole⟩-N-CH$_3$ | 4 |
| (−) | —CH$_2$N$^+$ ⟨triazole⟩-N-CH$_3$ | 7 |
| (−) | —CH$_2$N$^+$ ⟨imidazole⟩-NCH$_2$CONH$_2$ | 7 |
| (−) | —CH$_2$N$^+$ ⟨pyrazole⟩ N-CH$_3$ | 3 |
| (−) | —CH$_2$N$^+$ ⟨imidazole⟩-N—CH$_2$SOCH$_3$ | 4 |
| K | —CH$_2$N$^+$ ⟨imidazole⟩-NCH$_2$SO$_3^-$ | 4 |
| (−) | —CH$_2$N$^+$ ⟨triazole⟩ NCH$_3$ | 3 |
| K | —CH$_2$N$^+$ ⟨imidazole⟩ | 3 |
| K | —CH$_2$N$^+$ ⟨pyridine⟩-CO$_2^-$ | 3 |
| (−) | —CH$_2$N$^+$ ⟨imidazole⟩ NCH$_2$CH$_2$OH | 4 |
| (−) | —CH$_2$N$^+$ ⟨pyridine⟩-NH$_2$ | 4 |
| (−) | —CH$_2$N$^+$ ⟨pyridine, CH$_2$S(O)CH$_3$, NH$_2$⟩ | 3 |
| (−) | —CH$_2$N$^+$ ⟨pyridine⟩-CH$_2$OH | 3 |
| (−) | —CH$_2$N$^+$ ⟨pyridine, CH$_2$OH, NH$_2$⟩ | 4 |
| (−) | —OCH$_2$CH$_2$N$^+$ ⟨pyridine⟩-NH$_2$ | 7 |
| (−) | —SCH$_2$CH$_2$N$^+$ ⟨pyridine⟩-NH$_2$ | 7 |
| (−) | —SO$_2$CH$_2$CH$_2$N$^+$ ⟨pyridine⟩-NH$_2$ | 7 |
| (−) | —CH$_2$OCH$_2$CH$_2$N$^+$ ⟨pyridine⟩-NH$_2$ | 4 |

TABLE I-continued
| | | |
|---|---|---|
| (—) | 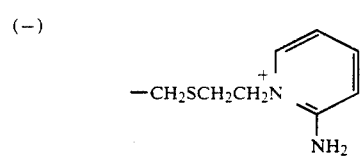 | 4 |
| (—) | 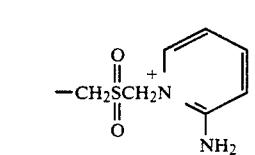 | 4 |
| (—) | 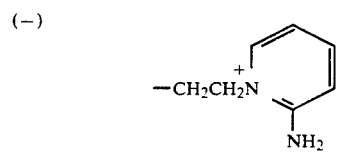 | 1 |
| (—) | 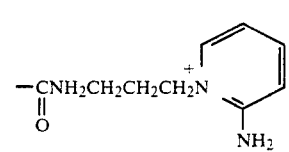 | 7 |
| (—) | 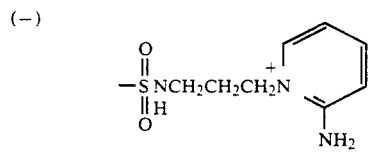 | 4 |
| (—) | 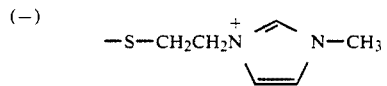 | 7 |
| (—) | 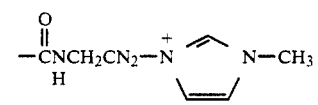 | 3 |
| (—) | 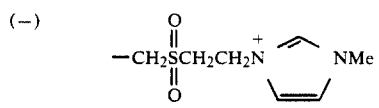 | 3 |
| (—) | 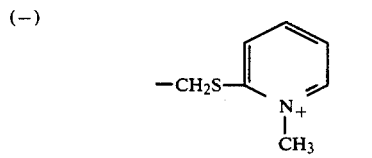 | 3 |
| (—) | 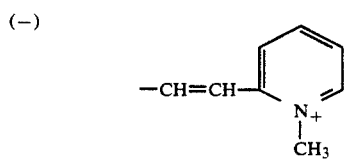 | 3 |
| H | 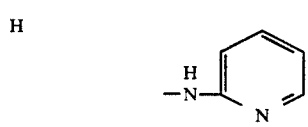 | 3 |
TABLE I-continued
| | | |
|---|---|---|
| (—) | 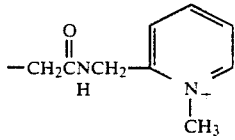 | 3 |
| (—) | 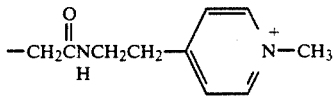 | 3 |
| (—) | 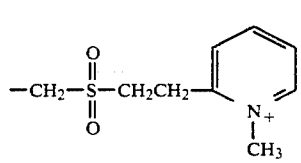 | 3 |
| (—) | 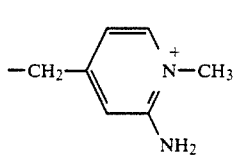 | 3 |
| (—) | 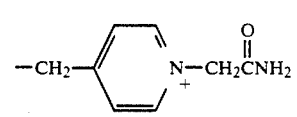 | 2 |
| K | 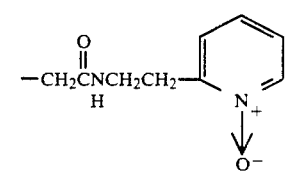 | 3 |
| K | 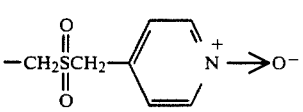 | 3 |
| (—) | 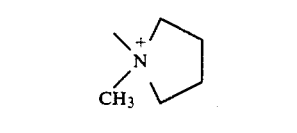 | 7 |
| (—) | 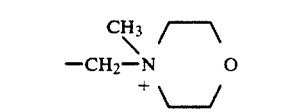 | 3 |
| (—) | 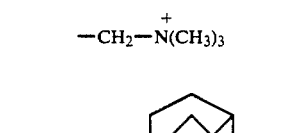 | 4 |
| (—) | 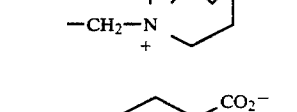 | 4 |
| K | 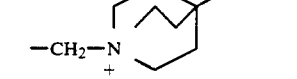 | 4 |

TABLE I-continued

| M | Rᵃ | Rᵃ Position | Rᵃ | Rᵃ Position |
|---|---|---|---|---|
| K | | | 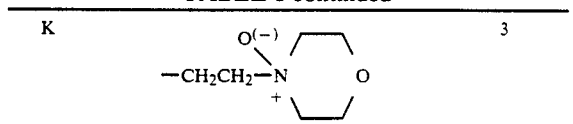 | 3 |
| (−) | | | 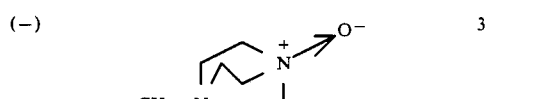 | 3 |
| (−) | | | 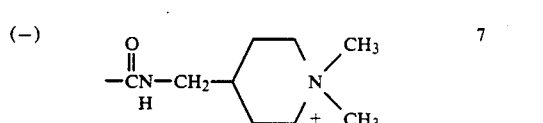 | 7 |
| (−) | CN | 7 | 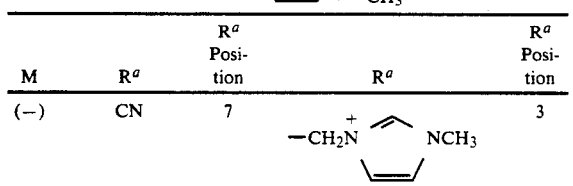 | 3 |
| (−) | SOCH₃ | 7 | 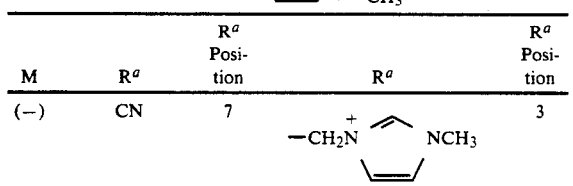 | 3 |
| (−) | CO₂K | 7 | 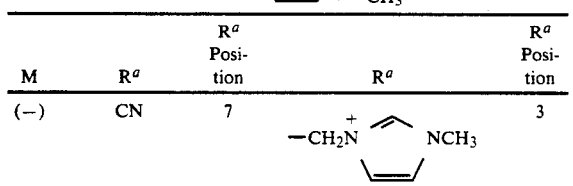 | 3 |
| (−) | SO₃K | 7 | 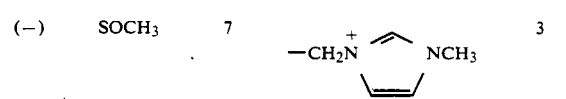 | 3 |
| (−) | 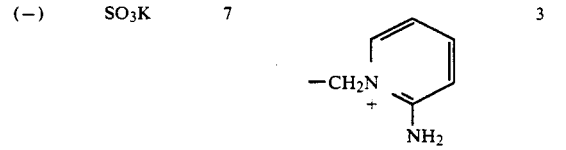 | 7 | 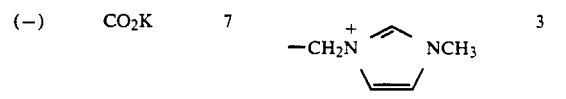 | 4 |
| (−) | SO₂CH₃ | 7 | 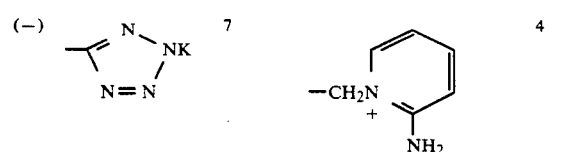 | 4 |
| (−) | CN | 7 | 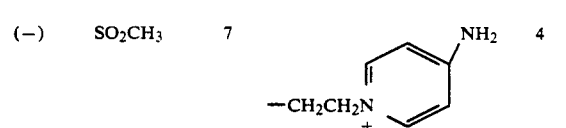 | 4 |
| (−) | CONH₂ | 7 | 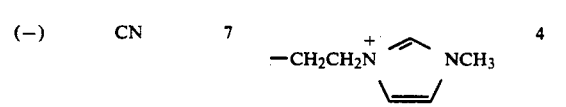 | 3 |
| (−) | CONH₂ | 7 | 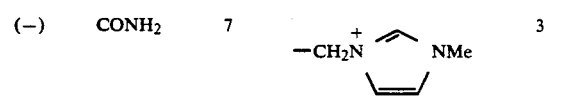 | 4 |
| (−) | 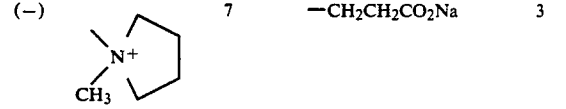 | 7 | −CH₂CH₂CO₂Na | 3 |
| Na | CN | 7 | 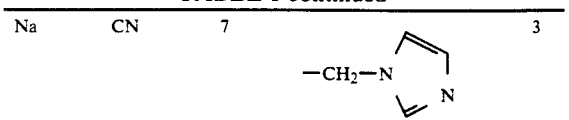 | 3 |
| (−) | SO₃K | 3 | 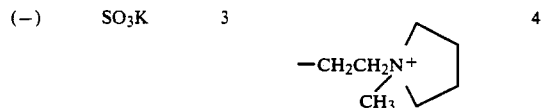 | 4 |
| (−) | CHO | 7 | 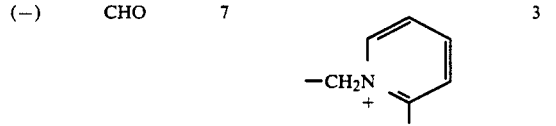 | 3 |

The carbapenem compounds of the present invention are useful per se and in their pharmaceutically acceptable salt and ester forms in the treatment of bacterial infections in animal and human subjects. The term "pharmaceutically acceptable ester of salt" refers to those salt and ester forms of the compounds of the present invention which would be apparent to the pharmaceutical chemist, i.e., those which are non-toxic and which would favorably affect the pharmacokinetic properties of said compounds, their palatability, absorption, distribution, metabolism and excretion. Other factors, more practical in nature, which are also important in the selection, are cost of the raw materials, ease of crystallization, yield, stability, hygroscopicity, and flowability of the resulting bulk drug. Conveniently, pharmaceutical compositions may be prepared from the active ingredients in combination with pharmaceutically acceptable carriers. Thus, the present invention is also concerned with pharmaceutical compositions and methods of treating bacterial infections utilizing as an active ingredient the novel carbapenem compounds of the present invention.

The pharmaceutically acceptable salts referred to above may take the form —COOM. The M may be an alkali metal cation such as sodium or potassium. Other pharmaceutically acceptable cations for M may be calcium, magnesium, zinc, ammonium, or alkylammonium cations such as tetramethylammonium, tetrabutylammonium, choline, triethylhydroammonium, meglumine, triethanolhydroammonium, etc.

The pharmaceutically acceptable salts referred to above may also include non-toxic acid addition salts. Thus, the Formula I compounds can be used in the form of salts derived from inorganic or organic acids. Included among such salts are the following: acetate, adipate, alginate, asparatate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalene-sulfonate, nicotinate, oxalate, pamoate, pectinate, persulfate, 3-phenylpropionate, picrate, pivalate, propionate, succinate, tartrate, thiocyanate, tosylate, and undecanoate.

The pharmaceutical acceptable esters of the novel carbapenem compounds of the present invention are such as would be readily apparent to a medicinal chemist, and include, for example, those described in detail in U.S. Pat. No. 4,309,438, Column 9, line 61 to Column 12, line 51, which is incorporated herein by reference. Included within such pharmaceutically accepable esters are those which are hydrolyzed under physiological conditions, such as pivaloyloxymethyl, acetoxymethyl, phthalidyl, indanyl and methoxymethyl, and those described in detail in U.S. Pat. No. 4,479,947, which is incorporated herein by reference.

The novel carbapenem compounds of the present invention may take the form COOM, where M is a readily removable carboxyl protecting group. Such conventional blocking groups consist of known ester groups which are used to protectively block the carboxyl group during the synthesis procedures described above. These conventional blocking groups are readily removable, i.e., they can be removed, if desired, by procedures which will not cause cleavage or other disruption of the remaining portions of the molecule. Such procedures include chemical and enzymatic hydrolysis, treatment with chemical reducing or oxidizing agents under mild conditions, treatment with a transition metal catalyst and a nucleophile, and catalytic hydrogenation. Broadly, such ester protecting groups include alkyl, substituted alkyl, benzyl, substituted benezyl, aryl, substituted aryl, allyl, substituted allyl and triorganosilyl. Examples of specific such ester protecting groups include benzhydryl, p-nitrobenzyl, 2-naphthylmethyl, allyl, 2-chloroallyl, benzyl, 2,2,2-trichloroethyl, trimethylsilyl, t-butyldimethylsilyl, t-butyldiphenylsilyl, 2-(trimethylsilyl)ethyl, phenacyl, p-methoxybenzyl, acetonyl, o-nitrobenzyl, 4-pyridylmethyl and t-butyl.

The compounds of the present invention are valuable antibacterial agents active against various Gram-positive and to a lesser extent Gram-negative bacteria and accordingly find utility in human and veterinary medicine. The antibacterials of the invention are not limited to utility as medicaments; they may be used in all manner of industry, for example: additives to animal feed, preservation of food, disinfectants, and in other industrial systems where control of bacterial growth is desired. For example, they may be employed in aqueous compositions in concentrations ranging from 0.1 to 100 parts of antibiotic per million parts of solution in order to destroy or inhibit the growth of harmful bacteria on medical and dental equipment and as bactericides in industrial applications, for example in waterbased paints and in the white water of paper mills to inhibit the growth of harmful bacteria.

The compounds of this invention may be used in any of a variety of pharmaceutical preparations. They may be employed in capsule, powder form, in liquid solution, or in suspension. They may be administered by a variety of means; those of principal interest include: topically or parenterally by injection (intravenously or intramuscularly).

Compositions for injection, a preferred route of delivery, may be prepared in unit dosage form in ampules, or in multidose containers. The compositions may take such forms as suspensions, solutions, or emulsions in oily or aqueous vehicles, and may contain formulatory agents. Alternatively, the active ingredient may be in powder form for reconstitution, at the time of delivery, with a suitable vehicle, such as sterile water. Topical applications may be formulated in hydrophobic or hydrophilic bases as ointments, creams, lotions, paints, or powders.

The dosage to be administered depends to a large extent upon the condition and size of the subject being treated as well as the route and frequency of administration, the parenteral route by injection being preferred for generalized infections. Such matters, however, are left to the routine discretion of the therapist according to principles of treatment well known in the anti-bacterial art. Another factor influencing the precise dosage regimen, apart from the nature of the infection and peculiar identity of the individual being treated, is the molecular weight of the chosen species of this invention.

The compositions for human delivery per unit dosage, whether liquid or solid, may contain from 0.1% to 99% of active material, the preferred range being from about 10–60%. The composition will generally contain from about 15 mg to about 1500 mg of the active ingredient; however, in general, it is preferable to employ a dosage amount in the range of from about 250 mg to 1000 mg. In parenteral administration, the unit dosage is usually the pure compound I in sterile water solution or in the form of a soluble powder intended for solution.

The preferred method of administration of the Formula I antibacterial compound is parenteral by i.v. infusion, i.v. bolus, or i.m. injection.

For adults, 5–50 mg of Formula I antibacterial compounds per kg of body weight given 2, 3, or 4 times per day is preferred. Preferred dosage is 250 mg to 1000 mg of the Formula I antibacterial given two (b.i.d.) three (t.i.d.) or four (q.i.d.) times per day. More specifically, for mild infections a dose of 250 mg t.i.d. or q.i.d. is recommended. For moderate infections against highly susceptible gram positive organisms a dose of 500 mg t.i.d. or q.i.d. is recommended. For severe, life-threatening infections against organisms at the upper limits of sensitivity to the antibiotic, a dose of 1000 mg t.i.d. or q.i.d. is recommended.

For children, a dose of 5–25 mg/kg of body weight given 2, 3, or 4 times per day is preferred; a dose of 10 mg/kg t.i.d. or q.i.d. is usually recommended.

Antibacterial compounds of Formula I are of the broad class known as carbapenems or 1-carbadethiapenems. Naturally occuring carbapenems are susceptible to attack by a renal enzyme known as dehydropeptidase (DHP). This attack or degradation may reduce the efficacy of the carbapenem antibacterial agent. The compounds of the present invention, on the other hand, are significantly less subject to such attack, and therefore may not require the use of a DHP inhibitor. However, such use is optional and contemplated to be part of the present invention. Inhibitors of DHP and their use with carbapenem antibacterial agents are disclosed in the prior art [see European Patent Applications No. 79102616.4 filed Jul. 24, 1979 (Patent No. 0 007 614); and No. 82107174.3, filed Aug. 9, 1982 (Publication No. 0 072 014)].

The compounds of the present invention may, where DHP inhibition is desired or necessary, be combined or used with the appropriate DHP inhibitor as described in the aforesaid patents and published application. Thus, to the extent that the cited European patent applications 1) define the procedure for determining DHP susceptibility of the present carbapenems and 2) disclose suitable inhibitors, combination compositions and methods of treatment, they are incorporated herein by reference. A preferred weight ratio of Formula I compound: DHP inhibitor in the combination compositions is about 1:1. A preferred DHP inhibitor is 7-(L-2-amino-2-carboxyethylthio)-2-(2,2-dimethylcyclopropanecarboxamide)-2-heptenoic acid or a useful salt thereof.

The benzocoumarin rings of formula I is not numbered in this text and claims as convention dictates. In the examples, conventional numbering of these rings is employed per the formula:

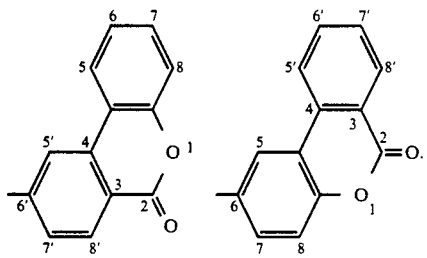

EXAMPLE 1

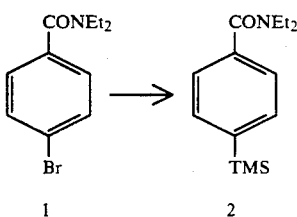

Chlorotrimethylsilane (10.4 mL, 81.9 mmol, 3.0 eq) was added to a stirred solution of 1 (7.0 g, 27.3 mmol) in dry THF (103 mL) at −78° C. under N$_2$. Tert-butyllithium (23.1 mL, 30 mmol, 1.1 eq) was added dropwise at −78° C. over 45 minutes. The reaction mixture was warmed to 0° C. with an ice bath and then quenched with saturated ammonium chloride solution (25 mL). After removal of THF in vacuo the reaction mixture was poured into ether (400 mL) and washed with water, saturated sodium bicarbonate solution (2×50 mL), water, and brine. The ethereal layer was dried (MgSO$_4$), filtered, and evaporated in vacuo. Purification using flash chromatography (20% EtOAc/hex) afforded 5.7 g (87%) of aryl silane 2, a white solid.

$^1$H-NMR for 2 [400 MHz, CDCl$_3$, rotamers]: δ 0.24 (s, 9H), 1.08 (broad s, 3H), 1.21 (broad s, 3H), 3.23 (broad s, 2H), 3.51 (broad s, 2H), 7.30 (d, J=8.1 Hz, 2H), 7.50 (d, J=8.1 Hz, 2H).
IR(CHCl$_3$): 3010, 1615 cm$^{-1}$.

EXAMPLE 2

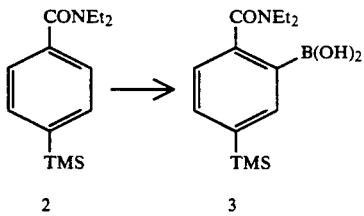

To a stirred solution of N,N,N',N'-tetramethylethylenediamine (2.7 mL, 17.6 mmol, 1.1 eq) in anhydrous THF (100 mL) at −78° C. under N$_2$ was added dropwise sec-butyllithium (13.0 mL, 16.8 mmol, 1.05 eq). After 15 minutes the yellow mixture was treated with a solution of 2 (4.0 g, 16.0 mmol) in dry THF (40 mL), and the resultant red mixture was stirred for 1 hour at −78° C. Trimethylborate (2.0 mL, 17.6 mmol, 1.1 eq) was added dropwise. The reaction flask was warmed to 0° C. with an ice bath and then stirred for 5 minutes. The green reaction mixture was quenched with 8% HCl solution (60 mL), stirred for 10 minutes, and the organic solvent concentrated in vacuo. The mixture was poured into ether and the ethereal layer was washed with water (2×), brine, dried (MgSO$_4$), filtered, and evaporated in vacuo. Purification using flash chromatography (5:3:1 EtOAc/acetone/H$_2$O) provided 3.77 g (80%) of boronic acid 3, a white foam.

$^1$H-NMR for 3 [200 MHz, CDCl$_3$, rotamers]: δ 0.27 (s, 9H), 0.88 to 1.16 (m, 6H), 3.27 to 3.36 (m, 4H), 7.28 (d, J=6.4 Hz, 1H), 7.52 (d, J=7.6 Hz, 1H), 8.15 (s, 1H).
IR(CHCl$_3$): 2960, 1615, 1601 cm$^{-1}$.

EXAMPLE 3

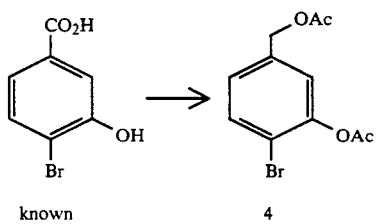

To a solution of bromo-hydroxybenzoic acid (1.0 g, 4.6 mmol) in dry THF (30 mL) cooled to 0° C. under N$_2$ was added THF.BH$_3$ (13.8 mL, 13.8 mmol, 3.0 eq) dropwise. Upon completion of addition, the ice bath was removed and the solution heated to reflux for 30 minutes. The reaction vessel was cooled to 0° C. and quenched by dropwise addition of MeOH (30 mL) containing triethylamine (1 mL). The solvents were then removed in vacuo. The residual was dissolved in MeOH and the MeOH removed in vacuo (3×). The remaining solid was dissolved in pyridine (10 mL) and treated with acetic anhydride (10 mL). After being stirred at ambient temperature for one hour the contents of the reaction vessel were poured into Et$_2$O and washed with 2N HCl solution (2×), H$_2$O (1×), 2N HCl (2×), and brine. The ethereal layer was dried (MgSO$_4$), filtered and evaporated in vacuo. The residual oil was passed through a short plug of SiO$_2$ using EtOAc/hex (20%) as an eluent to provide 1.32 g (quantitative yield) of bis-acetate 4.

$^1$H-NMR (400 MHz, CDCl$_3$) δ 2.09 (s, 3H), 2.34 (s, 3H), 5.04 (s, 2H), 7.08–7.14 (m, 2H), 7.57 (d, J=8.0 Hz, 1H).

EXAMPLE 4

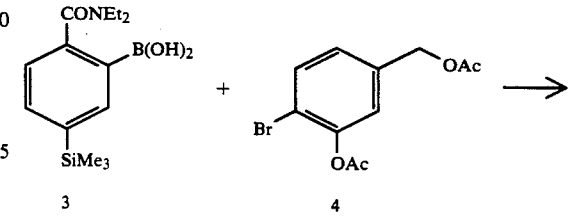

-continued

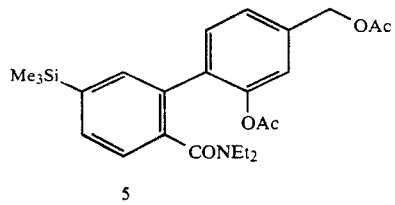

To boronic acid 3 (200.0 mg; 0.68 mmol) in toluene (5.0 mL) was added tetrakis(triphenylphosphine)palladium(0) (23.0 mg; 3 mol %), Na$_2$CO$_3$ (680 μL; 1.36 mmol; 2.0 eq) and arylbromide 5 (196.0 mg; 0.68 mmol; 1.0 eq) in ethanol (2.0 mL). The heterogeneous mixture was heated to reflux for 60 minutes under an atmosphere of nitrogen. The reaction mixture was then poured into Et$_2$O and washed with H$_2$O (3×), brine (2×), dried (MgSO$_4$), filtered and the solvent removed in vacuo. Purification by flash chromatography (40% EtOAc/hex) provided 147.0 mg (47%) of biphenyl 5.

$^1$H-NMR (400 MHz, CDCl$_3$, Rotamers) δ0.24 (s, 9H), 0.75 (t, J=6.5 Hz, 3H), 0.85 (t, J=6.5 Hz, 3H), 2.04 (s, 3H), 2.08 (s, 3H), 2.60–3.10 (broad, 3H), 3.55–3.85 (b, 1H), 5.08 (s, 2H), 7.13 (s, 1H), 7.20 (d, J=8.0 Hz, 1H), 7.33 (d, J=6.4 Hz, 1H), 7.39 (s, 1H), 7.41–7.48 (broad, 1H), 7.52 (d, J=6.4 Hz, 1H).

EXAMPLE 5

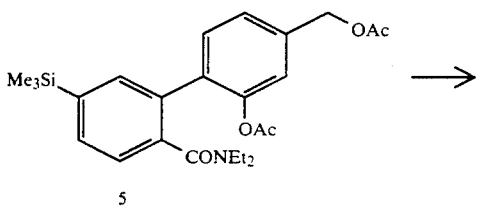

To a solution of biphenyl 5 (98.0 mg; 0.215 mmol) in dichloromethane (1 mL) at ambient temperature was added ICl (2.15 mL; 2.15 mmol; 10.0 eq) in dichloromethane dropwise slowly. The reaction mixture was stirred overnight. The following morning, the reaction mixture was poured into Et$_2$O, washed with saturated sodium thiosulfate solution, H$_2$O, and brine. The ethereal layer was dried (MgSO$_4$), filtered and solvent removed in vacuo to afford 110 mg (quantitative yield) of iodide 6.

$^1$H-NMR (200 MHz, CDCl$_3$, Rotamers) δ 0.70–0.91 (m, 6H), 2.10 (s, 3H), 2.15 (s, 3H), 2.60–3.10 (broad, 3H), 3.30–3.80 (broad, 1H), 5.10 (s, 2H), 7.10–7.29 (complex m, 3H), 7.42 (d, J=7.2 Hz, 1H), 7.67 (s, 1H), 7.78 (d, J=7.6 Hz, 1H).

EXAMPLE 6

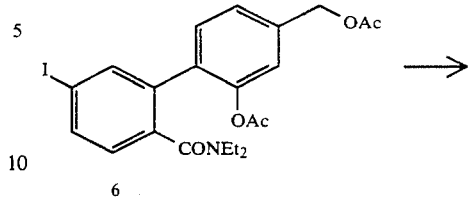

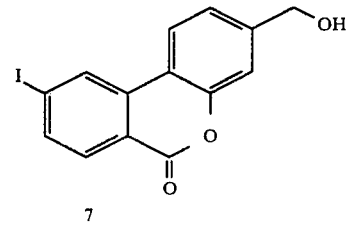

To a stirred solution of iodide 6 (109.0 mg, 0.215 mmol) in MeOH (8 mL) was added a 25% weight solution of NaOMe (250 μL, 1.15 mmol, 5.3 eq). Upon consumption of 6 as indicated by SiO$_2$ TLC (50% EtOAc/hex), the reaction mixture was poured into Et$_2$O and washed sequentially with saturated NH$_4$Cl solution, H$_2$O, and brine. After drying (MgSO$_4$), filtration and removal of the solvent in vacuo, the crude residue was suspended in toluene (10 mL) and heated to reflux in the presence of a catalytic amount of p-toluenesulfonic acid. Upon consumption of the intermediate diol as indicated by SiO$_2$ TLC (50% EtOAc/hex), the reaction mixture was poured into Et$_2$O and washed sequentially with saturated NaHCO$_3$ solution, H$_2$O and brine. Drying (MgSO$_4$), filtration and removal of the solvent in vacuo provided 75.7 mg (quantitative yield) of the benzocoumarin 7, a white solid.

$^1$H-NMR (400 MHz, D$_6$ DMSO) δ 4.18 (s, 2H), 6.88 (m, 2H), 7.53 (m, 2H), 7.85 (m, 1H), 8.35 (s, 1H).

EXAMPLE 7

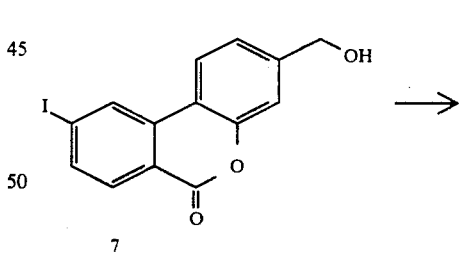

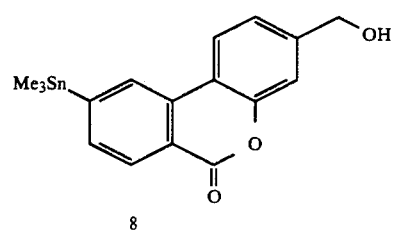

To iodide 7 (510.0 mg, 1.45 mmol) in toluene (25 mL) was added tetrakis(triphenylphosphine)palladium(0) (84.0 mg, 0.0725 mmol, 5 mol %), triphenylphosphine (11.0 mg, 0.044 mmol, 3 mol %) and hexamethylditin (327.6 mg, 1.59 mmol, 1.1 eq). Nitrogen was then bubbled through the solution for approximately 5 minutes before the mixture was heated to reflux under nitrogen. Upon consumption of iodide 7 as indicated by SiO2 TLC (50% EtOAc/hex), the reaction mixture was poured into EtOAc and washed with saturated NaHCO3 (2×), H2O (1×) and brine (1×). The organic layer was dried (MgSO4), filtered and evaporated in vacuo to provide a tan solid which was repeatedly precipitated from EtOAc/hex to provide 458 mg (81%) of stannane 8, a tan solid.

$^1$H-NMR (400 MHz, D6 Acetone) δ 0.41 (s, 9H), 4.75 (s, 2H), 7.36–7.39 (m, 2H), 7.82 (d, J=7.6 Hz, 1H), 8.22 (d, J=7.6 Hz, 1H), 8.34 (d, J=8.0 Hz, 1H), 8.55 (s, 1H).

EXAMPLE 8

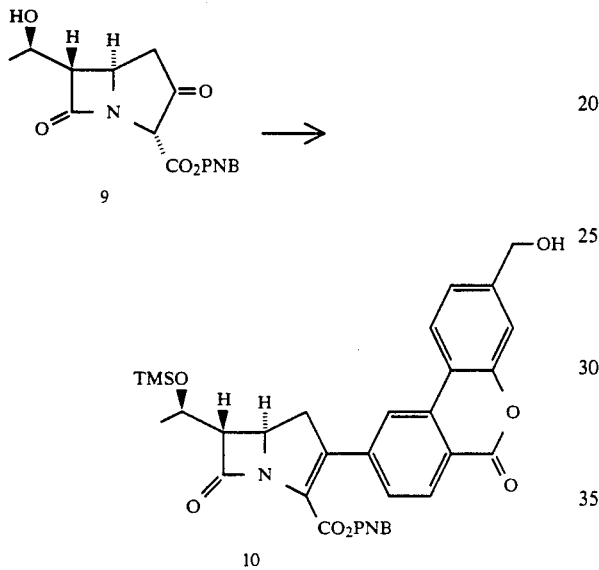

To a stirred solution of the bicyclic β-keto ester 9 (134.6 mg, 0.386 mmol) in dry THF (2.0 mL) at −78° C. under N2 was added diisopropylamine (60.0 μL, 0.43 mmol, 1.1 eq). The resultant yellow mixture was stirred for 10 minutes before trifluoromethanesulfonic anhydride (71.0 μL, 0.43 mmol, 1.1 eq) was added. After 15 minutes triethylamine (60.0 μL, 0.43 mmol, 1.1 eq), followed by the trimethylsilyl trifluoromethanesulfonate (82.0 μL, 0.43 mmol, 1.1 eq), was added and the reaction mixture was stirred for 20 minutes.

The reaction mixture was then treated sequentially with anhydrous N-methylpyrrolidinone (2.0 mL), the Pd2(dba)3·CHCl3 catalyst (8.0 mg, 2.0 mol %), the aryl stannane 8 (100.0 mg, 0.257 mmol, 0.66 eq), and zinc chloride (0.19 mL, 0.257 mmol, 0.66 eq). The low temperature bath was then removed and the reaction vessel was placed in a warm water bath to quickly reach ambient temperature. The solution was stirred for 15 minutes at ambient temperature.

The reaction was then poured into ether and washed with saturated sodium bicarbonate solution, water and brine. The organic layer was dried (MgSO4), filtered and evaporated in vacuo. Purification using flash chromatography (65% EtOAc/hex) provided 146 mg (90%) of the coupled product 10.

$^1$H-NMR (400 MHz, CDCl3) δ 0.14 (s, 9H), 1.29 (d, J=6.2 Hz, 3H), 2.34 (t, J=6.0 Hz, 1H), 3.25–3.34 (complex m, 2H), 3.41 (½ ABX, J$_{AB}$=18.5 Hz, J$_{AX}$=8.9 Hz, 1H), 4.23–4.29 (m, 1H), 4.35 (dt, J=10.0, 3.0 Hz, 1H), 4.74 (d, J=5.8 Hz, 2H), 5.22 (ABq, J$_{AB}$=13.5 Hz, Δυ$_{AB}$=69.8 Hz, 2H), 7.23 (d, J=8.0 Hz, 1H), 7.28 (s, 1H), 7.40 (d, J=8.8 Hz, 2H), 7.44 (dd, J=8.3, 1.6 Hz, 1H), 7.74 (d, J=8.2 Hz, 1H), 7.95 (d, J=1.5 Hz, 1H), 7.99 (d, J=8.7 Hz, 2H), 8.27 (d, J=8.3 Hz, 1H). I.R. (CHCl3) 3640–3580, 3020, 2960, 1780, 1730, 1610, 1540 cm$^{-1}$.

U.V. (CH3CN) λ=322 nm; ε=13,500; λ=305 nm, ε=16,900.

EXAMPLE 9

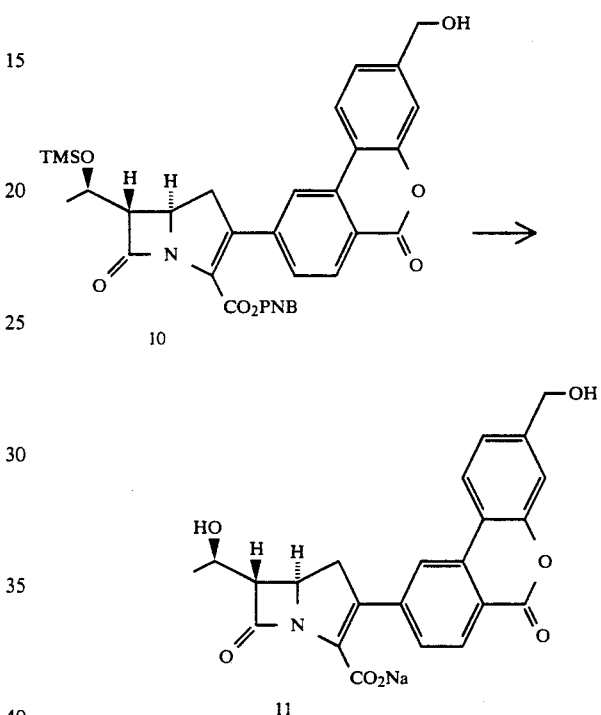

To a stirred solution of 10 (66.0 mg, 0.105 mmol) in THF/H2O (9 mL, 2:1) cooled to 0° C. was added HCl in Et2O (52.0 μL, 0.052 mmol, 0.5 eq). After ten minutes at 0° C., a solution of NaHCO3 (210 μL, 0.21 mmol, 2.0 eq) was added followed by 10% Pd/C (6.6 mg, 10 wt. %). The ice bath was removed and the reaction vessel placed under an atmosphere of H2 employing a balloon. After 45 minutes, the H2 atmosphere was replaced by N2 and the stirring was continued for an additional 15 minutes. The reaction mixture was then filtered through a pad of Celite using H2O as the eluent. The THF was removed in vacuo and the remaining H2O lyophilized at 0° C. The resulting solid was purified using reverse phase prep-plate chromatography (6:1 H2O/CH3CN) to afford 35.7 mg (76.6%) of carbapenem 11.

$^1$H-NMR (400 MHz, D2O/CD3CN 2:1) δ 1.61 (d, J=6.5 Hz, 3H), 3.50 (½ ABX, J$_{AB}$=16.5 Hz, J$_{AX}$=9.8 Hz, 1H), 3.81–3.88 (complex m, 2H), 4.51–4.57 (m, 1H), 4.65 (dt, J=9.7, 3.2 Hz, 1H), 5.02 (s, 3H), 7.67 (s, 1H), 7.71 (d, J=8.3 Hz, 1H), 7.92 (d, J=8.3 Hz, 1H), 8.46 (d, J=8.2 Hz, 1H), 8.48–8.51 (m, 2H).

I.R. (KBr) 1755, 1715, 1610 cm$^{-1}$.

U.V. (MOPS BUFFER) λ=330 nm, ε=14,700; λ$_{ext}$=340 nm, ε$_{ext}$=10,500.

EXAMPLE 10

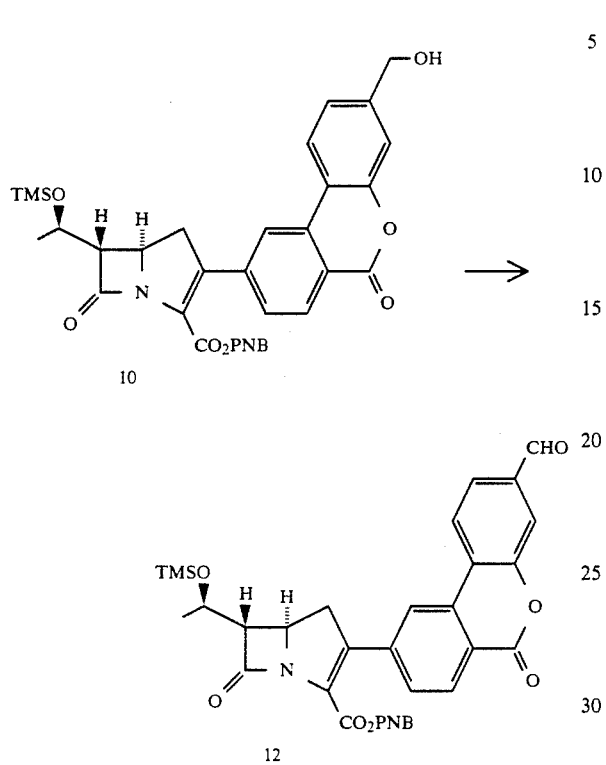

10

12

A stirred solution of 10 (33.0 mg, 0.0526 mmol), N-methylmorpholine-N-oxide (9.2 mg, 0.0788 mmol, 1.5 eq), and powdered 4 Å molecular sieves (26.0 mg, 500 mg/mmol) in dry dichloromethane (1.0 mL) was treated with tetrapropylammonium perruthenate (1.0 mg, 5.0 mol %) at room temperature under $N_2$. After 20 minutes, an additional 0.5 mg of "TPAP" was added to drive the reaction to completion. The reaction mixture was stirred for an additional 5 minutes before the resulting black mixture was filtered through a short-column of silica gel using 70% EtOAc/hex as an eluant. The filtrate was evaporated in vacuo to afford 21.0 mg (64%) of aldehyde 12. $^1$H-NMR (400 MHz, $CDCl_3$) δ 0.14 (s, 9H), 1.29 (d, J=6.3 Hz, 3H), 3.27-3.36 (complex m, 2H), 3.43 (½ ABX, $J_{AB}$=18.3 Hz, $J_{AX}$=8.7 Hz, 1H), 4.24-4.30 (m, 1H), 4.37 (dt, J=10.0, 2.8 Hz, 1H), 5.28 (ABq, $J_{AB}$=14.2 Hz, $\Delta\nu_{AB}$=68.1 Hz, 2H), 7.50 (d, J=8.6 Hz, 2H), 7.58 (dd, J=8.3, 1.5 Hz, 1H), 7.80-7.83 (m, 2H), 8.04-8.11 (m, 3H), 8.18 (s, 1H), 8.37 (d, J=8.4 Hz, 1H), 10.05 (s, 1H).

I.R. ($CHCl_3$) 3030, 2970, 1785, 1740, 1705, 1610, 1525.
U.V. ($CH_3CN$) λ=320 nm, ε=20,400; λ=291 nm, ε=26,500.

EXAMPLE 11

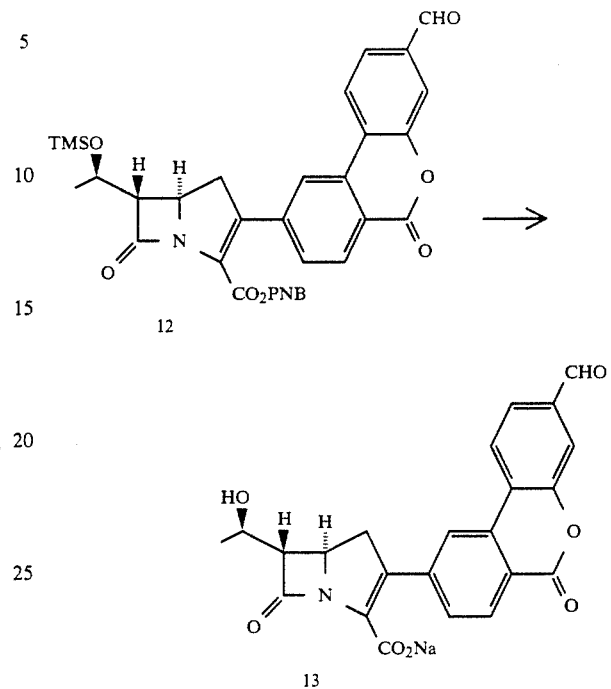

12

13

From 12 (21.0 mg, 0.0340 mmol) employing the general deprotection procedure as described for compound 10, was provided 4.6 mg (30%) of carbapenem 13.

$^1$H NMR (400 MHz, 2:1 $D_2O/CD_3CN$) δ 1.64 (d, J=6.3 Hz, 3H), 3.54 (½ ABX, $J_{AB}$=16.5 Hz, $J_{AX}$=9.9 Hz, 1H), 3.85-3.92 (complex m, 2H), 4.53-4.60 (m, 1H), 4.66-4.72 (m, 1H), 8.07 (d, J=8.1 Hz, 1H), 8.23 (d, J=1.4 Hz, 1H), 8.29 (d, J=8.1 Hz, 1H), 8.59 (d, J=8.4 Hz, 1H), 8.64 (s, 1H), 8.74 (d, J=8.1 Hz, 1H), 10.37 (s, 1H).

I.R. (KBr) 1730, 1695, 1610 cm$^{-1}$.
U.V. (MOPS BUFFER) λ=302 nm, ε=18,000; $\lambda_{ext}$=315 nm, $\epsilon_{ext}$=8,500.

EXAMPLE 12

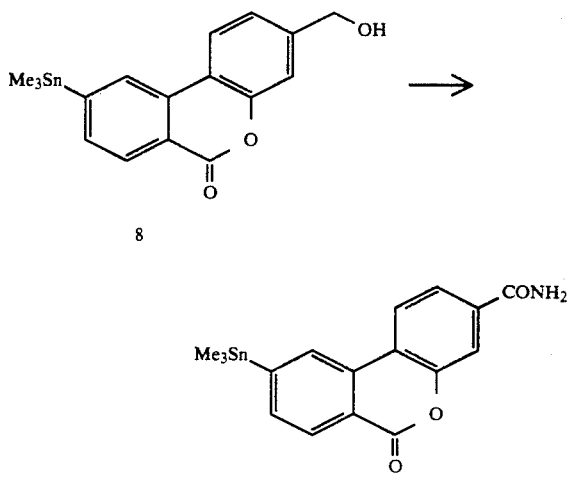

8

14

To a stirred solution of alcohol 8 (100.0 mg, 0.257 mmol) dissolved in anhydrous pyridine (1.0 mL) was added a solution of $^nBu_4NMO_4$ (123.0 mg, 0.342 mmol, 1.33 eq) in anhydrous pyridine (1.0 mL) dropwise. After 15 minutes the reaction mixture was poured into $Et_2O$ and washed sequentially with $NaHSO_3$ solution, 1N HCl solution, water and brine. The ethereal layer was dried ($MgSO_4$), filtered and evaporated in vacuo to provide the crude acid which was not isolated but instead dissolved in THF (6.5 mL) and $CH_3CN$ (1.5 mL) and sequentially treated with 1-(3-dimethylaminopropyl)-3-ethylcarbodiimide hydrochloride (98.5 mg, 0.514 mmol, 2 eq), 1-hydroxybenzotriazole hydrate (104.2 mg, 0.771 mmol, 3 eq) and ethanolic ammonia (500 µL, 1.28 mmol, 5 eq). The resulting milky white solution was stirred for approximately 1 hour before being quenched with saturated ammonium chloride. After removal of the THF and $CH_3CN$ in vacuo, the residual was poured into $Et_2O$ and washed with $H_2O$ and brine. The ethereal layer was dried ($MgSO_4$), filtered and evaporated in vacuo. Recrystallization provided 25.0 mg of pure 14. Flash chromatography of the mother liquor (100% EtOAc/hex) provided another 22.0 mg of 14 totaling 45% yield.

$^1$H NMR (200 MHz, CDCl$_3$) δ 0.43 (s, 9H), 5.70–6.30 (broad, 2H), 7.75–7.90 (complex m, 3H), 8.20 (d, J=8.3 Hz, 1H), 8.27 (s, 1H), 8.32 (d, J=7.7 Hz, 1H).

I.R. (CHCl$_3$) 3520, 3420, 3020, 2920, 1730, 1680, 1600 cm$^{-1}$.

EXAMPLE 13

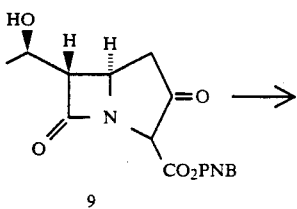

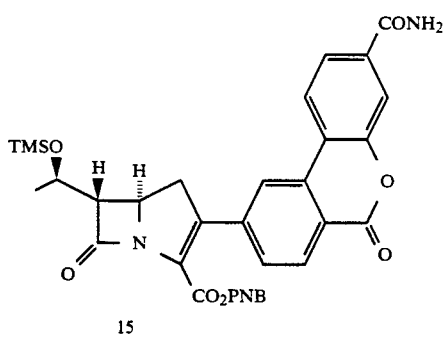

Compound 15 (50.6 mg, 70% yield) was obtained according to the general coupling procedure described for the manufacture of compound 10, except that stannane 14 was employed rather than stannane 8.

$^1$H NMR (300 MHz, CDCl$_3$) δ 0.14 (s, 9H), 1.30 (d, J=6.2 Hz, 3H), 3.25–3.37 (complex m, 2H), 3.45 (½ ABX, J$_{AB}$=18.5, J$_{AX}$=8.9 Hz, 1H), 4.23–4.32 (m, 1H), 4.37 (dt, J=9.9, 2.8 Hz, 1H), 5.25 (ABq, J$_{AB}$=13.6 Hz, Δv$_{AB}$=49.8 Hz, 2H), 5.85–6.10 (broad, 1H), 6.35–6.60 (broad, 1H), 7.45 (d, J=8.8 Hz, 2H), 7.52 (dd, J=8.2, 1.5 Hz, 1H), 7.71–7.74 (m, 2H), 7.89 (d, J=8.2 Hz, 1H), 8.03–8.07 (m, 3H), 8.29 (d, J=8.2 Hz, 1H).

I.R. (CHCl$_3$) 3520, 3420, 3020, 2960, 1780, 1730, 1680, 1610 cm$^{-1}$.

U.V. (CH$_3$CN) λ=310 nm, ε=17,400

EXAMPLE 14

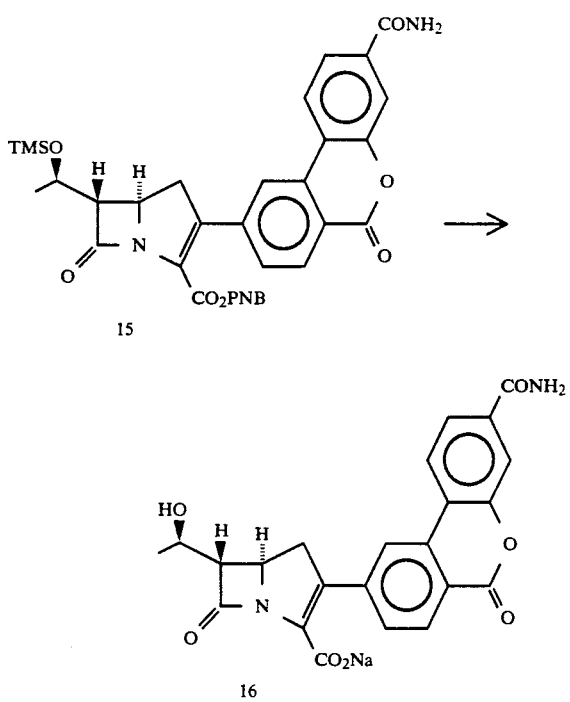

From 15 (25.0 mg, 0.039 mmol) employing the general deprotection procedure as described for compound 10, was provided 12.5 mg (70%) of carbapenem 16.

$^1$H-NMR (400 MHz, 2:1 D$_2$O/CD$_3$CN) δ 1.62 (d, J=6.5 Hz, 3H), 3.52 (½ ABX, J$_{AB}$=15.7 Hz, J$_{AX}$=9.1 Hz, 1H), 3.83–3.90 (complex m, 2H), 4.54–4.58 (m, 1H), 4.67 (t, J=8.0 Hz, 1H), 8.01 (d, J=8.2 Hz, 1H), 8.13 (s, 1H), 8.16 (d, J=8.4 Hz, 1H), 8.54–8.58 (m, 2H), 8.61 (d, J=8.4 Hz, 1H).

I.R. (KBr) 1725, 1670, 1600.

U.V. (MOPS BUFFER) λ=308 nm, ε=15,000; λ$_{ext}$=342 nm, ε$_{ext}$=9,400.

EXAMPLE 15

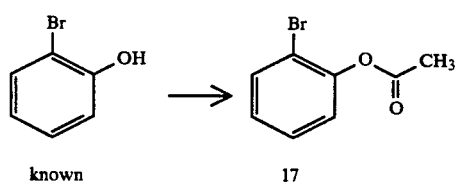

To o-bromophenol (500 mg, 2.89 mmol) in pyridine (5 mL) was added acetic anhydride (5 mL). Upon consumption of the starting material by SiO$_2$ TLC, the solvents were removed in vacuo to provide 621.0 mg (quantitative yield) of aryl bromide 17.

$^1$H-NMR (200 MHz, CDCl$_3$) δ 2.35 (s, 3H), 7.08–7.18 (m, 2H), 7.25–7.40 (m, 1H), 7.58–7.65 (m, 1H).

EXAMPLE 16

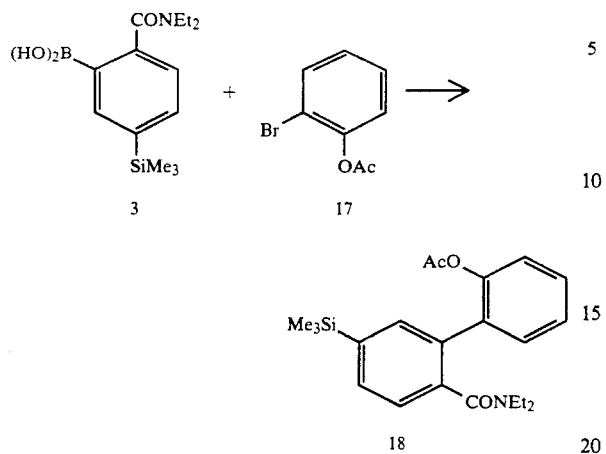

From 3 (70.0 mg, 0.24 mmol) and 17 (51.0 mg, 0.24 mmol) following the Suzuki procedure as described for the manufacture of compound 5 was provided 44.0 mg (48%) of biphenyl 18.

$^1$H-NMR (200 MHz, CDCl$_3$, Rotamers) δ 0.28 (s, 9H), 0.72-0.80 (complex m, 6H), 2.09 (s, 3H), 2.60-3.90 (broad, 4H), 7.13-7.60 (complex m, 7H).

I.R. (CHCl$_3$) 3000, 2860, 2800, 1760, 1740, 1610 cm$^{-1}$.

EXAMPLE 17

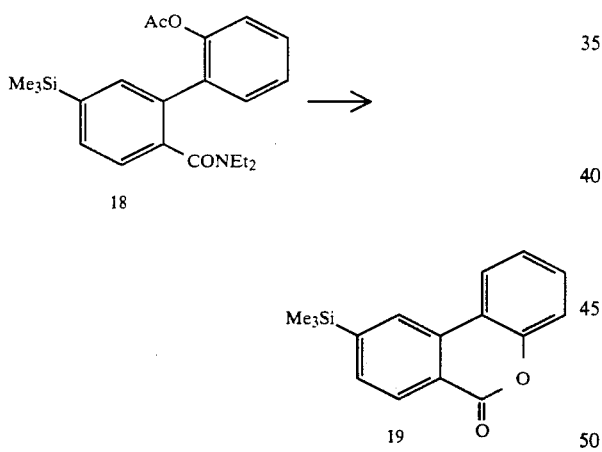

To a stirred solution of biphenyl 18 (161 mg, 0.42 mmol) in MeOH (5 mL) was added a 25% weight solution of NaOMe (9.0 μL, 0.042 mmol, 10 mol %). After approximately one hour, toluene was added (15 mL) followed by TsOH.H$_2$O (16.0 mg, 0.084 mmol, 20 mol %). The reaction mixture was then heated to reflux under a Dean-Stark apparatus for 20 minutes. The reaction mixture was then poured into Et$_2$O and washed with saturated sodium bicarbonate solution (3×) and brine (2×), dried (MgSO$_4$), filtered and the solvent removed in vacuo. Purification by flash chromatography (15% EtOAc/hex) provided 71.5 mg (63%) of benzocoumarin 19, a white crystalline solid.

$^1$H-NMR (200 MHz, CDCl$_3$) δ 0.39 (s, 9H), 7.31-7.52 (complex m, 3H), 7.73 (d, J=8.7 Hz, 1H), 8.14 (d, J=8.0 Hz, 1H), 8.27 (s, 1H), 8.35 (d, J=7.7 Hz, 1H).

I.R. (CHCl$_3$) 3010, 2980, 1728, 1600.

EXAMPLE 18

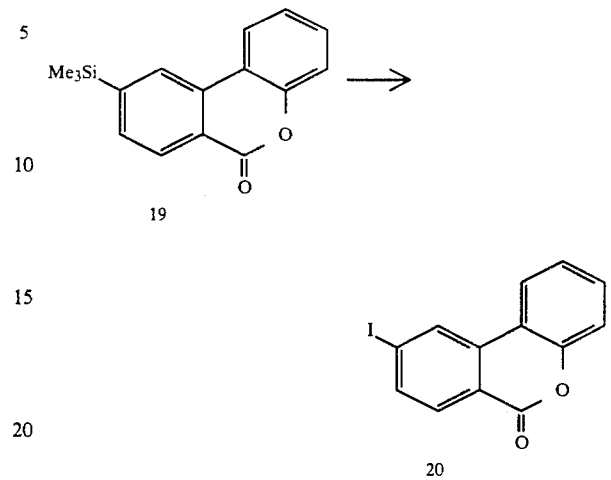

To a solution of 19 (71.5 mg, 0.266 mmol) in CH$_2$Cl$_2$ (1 mL) was added a solution of ICl (1.33 mL, 1.33 mmol, 5.0 eq) in CH$_2$Cl$_2$ over a period of one hour. Upon completion of addition, the reaction mixture was poured into Et$_2$O and washed with aqueous Na$_2$S$_2$O$_4$ solution, H$_2$O and brine. The ethereal layer was dried over MgSO$_4$, filtered and the solvent removal in vacuo to provide 85.6 mg (quantitative yield) of iodide 20.

$^1$H-NMR (200 MHz, CDCl$_3$) δ 7.32-7.40 (m, 2H), 7.48-7.56 (m, 1H), 7.92 (d, J=8.5 Hz, 1H), 8.05 (d, J=8.2 Hz, 1H), 8.09 (d, J=8.4 Hz, 1H), 8.50 (s, 1H).

I.R. (CHCl$_3$) 3010, 1730, 1600 cm$^{-1}$.

EXAMPLE 19

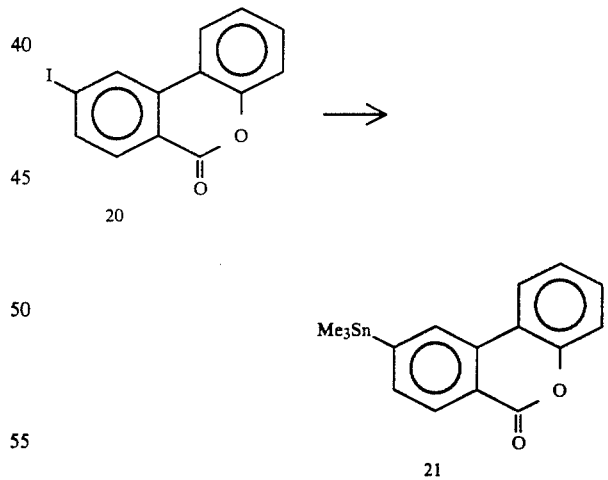

Iodide 20 (87.0 mg, 0.266 mmol) was dissolved in dry toluene (10 mL). Tetrakis(triphenylphosphine) palladium(0) (15 mg, 5 mol %) was added followed by triphenylphosphine (2 mg, 3 mol %) and hexamethylditin (96.0 mg, 0.29 mmol, 1.1 eq). Nitrogen was then bubbled through the solution for 5 minutes before the mixture was heated to reflux under nitrogen. Upon reaction completion (TLC), the mixture was poured into Et$_2$O and washed with saturated NaHCO$_3$ solution, H$_2$O and brine. The etheral layer was dried (MgSO$_4$), filtered and solvent remove in vacuo. Purification by flash chromatography (5% EtOAc/hex) provided 71 mg (74%) of stannane 21.

¹H-NMR (200 MHz, CDCl₃) δ 0.42 (s, 9H), 7.31–7.53 (complex m, 3H), 7.73 (d, J=7.8 Hz, 1H), 8.13 (d, J=7.8 Hz, 1H), 8.26 (s, 1H), 8.32 (d, J=7.8 Hz, 1H).

I.R. (CHCl₃) 3020, 2980, 2920, 1725, 1600 cm⁻¹.

EXAMPLE 20

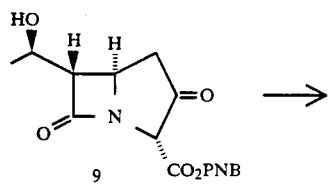

From 9 (103.0 mg, 0.30 mmol) and stannane 21 (71.0 mg, 0.2 mmol, 0.66 eq) following the general cross-coupling procedure as described for compound 10 was obtained 82.0 mg (69%) of 22.

¹H-NMR (400 MHz, CDCl₃) δ 0.14 (s, 9H), 1.30 (d, J=6.1 Hz, 3H), 3.26–3.33 (complex m, 2H), 3.41 (½ ABX, J$_{AB}$=18.3 Hz, J$_{AX}$=8.8 Hz, 1H), 4.25–4.28 (m, 1H), 4.33–4.38 (dt, J=9.8, 2.8 Hz, 1H), 5.24 (ABq, J$_{AB}$=13.5 Hz, Δv$_{AB}$=64.0 Hz, 2H), 7.26–7.35 (m, 2H), 7.43–7.87 (m, 3H), 7.87 (d, J=6.6 Hz, 1H), 8.04–8.07 (m, 2H), 8.33 (d, J=8.4 Hz, 1H).

I.R. (CHCl₃) 3020, 2960, 1760, 1730, 1610, 1520, cm⁻¹.

EXAMPLE 21

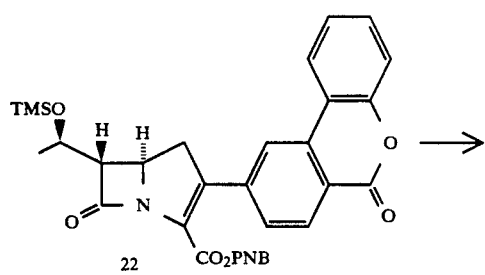

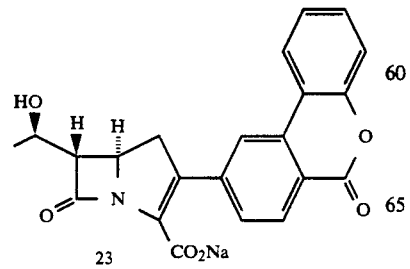

From 22 (41.0 mg, 0.068 mmol) following the general deprotection procedure as described for compound 11 was obtained 4.4 mg (15%) of carbapenem 23.

¹H-NMR (400 MHz, 2:1 D₂O/CDCl₃) δ 1.60 (d, J=6.3 Hz, 3H), 3.51 (½ ABX, J$_{AB}$=16.8 Hz, J$_{AX}$=10.0 Hz, 1H), 3.81–3.90 (complex m, 2H), 4.52–4.56 (m, 1H), 4.65 (t, J=8.0 Hz, 1H), 7.74 (d, J=8.1 Hz, 1H), 7.78–7.80 (m, 2H), 7.89–7.98 (m, 2H), 8.54–8.56 (m, 3H).

I.R. (KBr) 1780-1720 (broad), 1610 cm⁻¹.

U.V. (MOPS BUFFER) λ=328 nm, ε=10,500; λ$_{ext}$=338 nm, ε$_{ext}$=7,100.

EXAMPLE 22

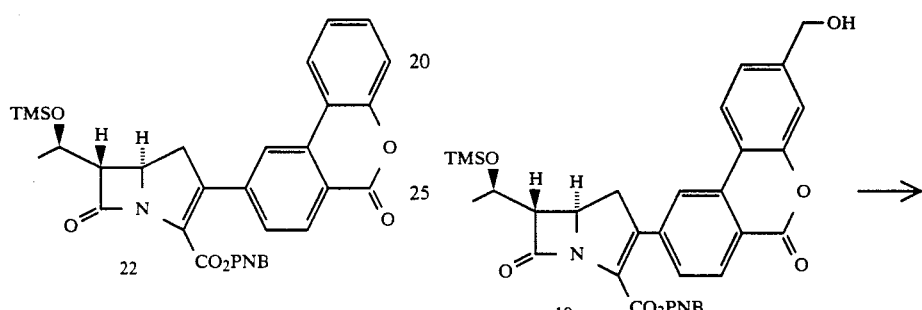

Compound 10 (146.0 mg, 0.23 mmol) was dissolved in CH₂Cl₂ (3.0 mL) and cooled to −78° C. under N₂. To this stirred solution was added N-methylimidazole (46.0 μL, 0.58 mmol, 2.5 eq) followed by trifluoromethanesulfonic anhydride (43.0 μL, 0.26 mmol, 1.1 eq). The reaction vessel was then warmed to −30° to −20° C. for approximately ten minutes before being poured into EtOAc containing some Et₂O. The organic layer was washed with H₂O (5×), dried (Na₂SO₄), filtered and evaporated in vacuo to provide 175.0 mg (89%) of compound 24 as a yellow foam.

¹H-NMR (400 MHz, CDCl₃) δ 0.14 (s, 9H), 1.30 (d, J=6.2 Hz, 3H), 3.29 (½ ABX, J$_{AB}$=18.3 Hz, J$_{AX}$=10.1 Hz, 1H), 3.37 (dd, J=5.8, 2.8 Hz, 1H), 3.45 (½ ABX, J$_{AB}$=18.6 Hz, J$_{AX}$=8.9 Hz, 1H), 4.00 (s, 3H), 4.23–4.31 (m, 1H), 4.37 (dt, J=10.3, 2.9 Hz, 1H), 5.21 (ABq, J$_{AB}$=13.4 Hz, Δv$_{AB}$=69.0 Hz, 2H), 5.47 (s, 3H), 7.20 (s, 1H), 7.27–7.46 (complex m, 7H), 7.78 (d, J=8.4 Hz, 1H), 7.92–7.95 (m, 2H), 8.17 (d, J=8.1 Hz, 1H), 9.39 (s, 1H).

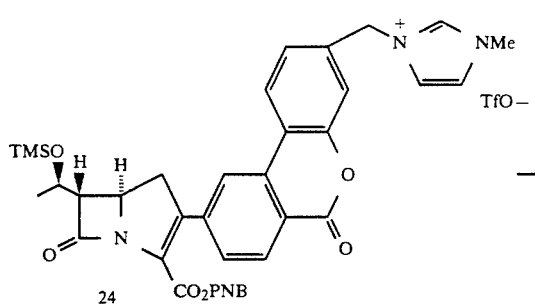

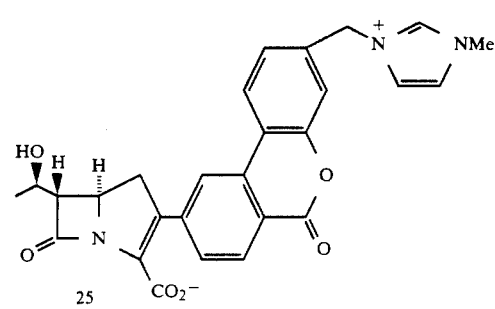

EXAMPLE 23

Compound 25 (8.5 mg, 33%), was obtained from compound 24 (44.0 mg, 0.05 mmol) employing the general deprotection procedure as described for compound 10 except that 2.0 equivalents of HCl in Et$_2$O at 0° C. for 1 hour were used to remove the silyl group and 3.0 equivalents of NaHCO$_3$ were used to neutralize the acid.

$^1$H-NMR (400 MHz, 2:1, D$_2$O/CDCl$_3$) 1.62 (d, J=6.1 Hz, 3H), 3.51 (½ ABX, J$_{AB}$=15.3 Hz, J$_{AX}$=9.7 Hz, 1H), 3.82–3.90 (complex m, 2H), 4.19 (s, 3H), 4.53–4.58 (m, 1H), 4.67 (dt, J=8.9, 2.4 Hz, 1H), 5.80 (s, 2H), 7.73 (s, 1H), 7.76 (d, J=8.0 Hz, 1H), 7.97 (d, J=8.0 Hz, 1H), 8.54–8.60 (complex m, 4H).

I.R. (KBr) 1760, 1725, 1600 cm$^{-1}$.

U.V. (MOPS BUFFER) λ=328 nm, ε=10,200; λ$_{ext}$=340 nm, ε$_{ext}$=7,600.

EXAMPLE 24

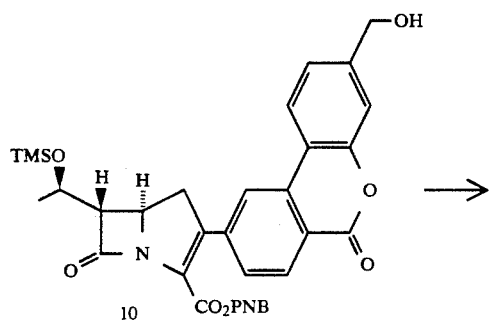

To a stirred solution of 10 (33.0 mg, 0.053 mmol) in CH$_2$Cl$_2$ (1.0 mL) cooled to −78° C. under N$_2$ was added collidine (8.3 μL, 0.063 mmol, 1.2 equiv.) followed by trifluoromethanesulfonic anhydride (9.7 μL, 0.058 mmol, 1.1 equiv.). After 35 minutes 4-methyl-1,2,4-triazole (9.6 mg, 0.116 mmol, 2.2 equiv.) was added. The reaction vessel was warmed to −30° C. and stirred for 30 minutes before being poured into EtOAc containing some Et$_2$O. The organic layer was washed with H$_2$O (4×), dried (Na$_2$SO$_4$), filter and evaporated in vacuo. The residual solid was dissolved in CH$_2$Cl$_2$ and precipitated using Et$_2$O (2×) to afford 26 mg (63%) of compound 26, a yellowish solid.

$^1$H NMR (400 MHz, CDCl$_3$) δ 0.13 (s, 9H), 1.28 (d, J=6.2 Hz, 3 H), 3.26 (½ ABX, J$_{AB}$=18.6 Hz, J$_{AX}$=10.2 Hz, 1H), 3.38 (dd, J=6.1, 3.0 Hz, 1H), 3.45 (½ ABX, J$_{AB}$=18.3 Hz, J$_{AX}$=9.9 Hz, 1H), 4.17 (s, 3H), 4.26 (m, 1H), 4.36 (t, J=9.8 Hz, 1H), 5.18 (ABq, J$_{AB}$=13.2 Hz, Δυ$_{AB}$=65.3 Hz, 2 H), 5.61 (s, 2 H), 7.33–7.44 (complex m, 6H), 7.75 (d, J=8.4 Hz, 1H), 7.86(s, 1H), 7.89 (d, J=8.8 Hz, 2 H), 8.06 (d, J=8.4 Hz, 1H), 8.74 (s, 1 H).

IR(CHCl$_3$) 1775, 1725, 1601 cm$^{-1}$.

U.V.(CH$_3$CN) λ=305 nm, ε=19,500.

EXAMPLE 25

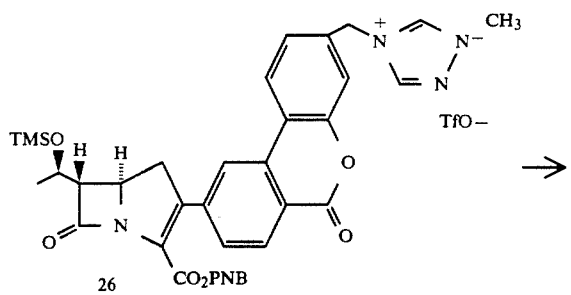

To a stirred solution of 26 (28 mg, 0.033 mmol) in 3 mL of THF/H$_2$O(2:1) cooled to 0° C. was added 1M HCl solution (16.6 μL, 0.016 mmol, 0.5 equiv.). After 16 minutes at 0° C., a 1M solution of NaHCO$_3$ (50.0 μL, 0.05 mmol 1.5 equiv.) was added followed by 10% Pd/C (8.4 mg, 30% wt.). The ice bath was removed and the vessel placed under an atmosphere of H₂ (balloon) for 1 hour. The reaction mixture was then filtered through celite using H₂O as a eluent. Lyophilization of the H₂O provided the crude solid which was purified by reverse-phase prep-plate chromatography (3:1 H₂O/CH₃CN) providing 11.9 mg (74%) of compound 27.

¹H NMR(200 MHz, 2:1 D₂O, CD₃CN) δ 1.68 (d, J=6.4 Hz, 3H), 3.50-3.68(m, 1H), 3.82-3.99 (m, 2H), 4.47 (s, 3H), 4.55-4.78 (m, 2H), 5.97 (s, 3H), 7.82-7.92 (m, 2H), 8.05 (d, J=8.7 Hz, 1H), 8.59-8.68 (m, 3H).

I.R. (KBr) 1755, 1730, 1610 cm⁻¹.

U.V. (MOPS BUFFER) λ=330 nm, ε=12,000, $\lambda_{ext}$=340 nm, $\epsilon_{ext}$=9,000.

What is claimed is:

1. A compound of the formula:

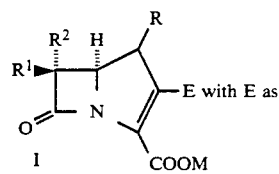

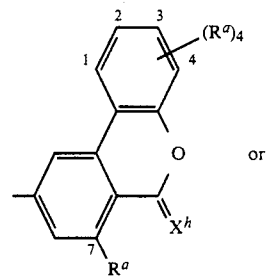
or

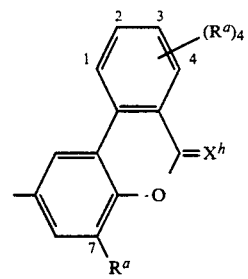

wherein:

R is H or CH₃;

$X^h$ is O or S;

R¹ and R² are independently H, CH₃—, CH₃CH₂—, (CH₃)₂CH—, HOCH₂—, CH₃CH(OH)—, (CH₃)₂C(OH)—, FCH₂CH(OH)—, F₂CHCH(OH)—, F₃CCH(OH)—, CH₃CH(F)—, CH₃CF₂—, or (CH₃)₂C(F)—;

R$^a$ are independently selected from the group consisting of hydrogen and the radicals set out below, provided that one but not more than one R$^a$ is a Type I substituent, the remaining non-hydrogen substituents being selected from Type II, and in total not more than four R$^a$ radicals are other than hydrogen:

I.

a) 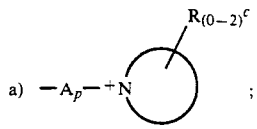

where

A is (CH₂)$_m$—Q—(CH₂)$_n$, where m is 0 to 6 and n is 1 to 6 and Q is a covalent bond, O, S, SO, SO₂, NH, —SO₂NH—, —NHSO₂—, —CONH—, —NHCO—, —SO₂N(C₁—C₄alkyl)—, —N(C₁—C₄alkyl)SO₂—, —CON(C₁—C₄alkyl)—, —N(C₁—C₄alkyl)CO—, —CH=CH—, —CO—, —OC(O)—, —C(O)O— or N(C₁—C₄alkyl) and (CH₂)$_m$ is attached to the benzocoumarinyl moiety;

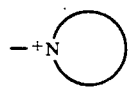

is a 5- or 6-membered monocyclic heterocycle or an 8-, 9- or 10-membered bicyclic heterocycle, the heterocycle containing a first nitrogen in an aromatic 5- or 6-membered first ring, with attachment of the heterocycle to A by way of said first nitrogen and said first nitrogen is quaternary by virtue of the attachment and ring bonds, with the first ring containing 0 or 1 of either O or S, with the first ring containing 0 to 3 additional nitrogen atoms, with the first ring optionally fused to a 3- or 4-membered moiety to form the optional second ring, with the the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

R$^c$ is R$^a$ as defined under II below, hydrogen, or —NR$^Y$R$^z$ (where R$^Y$ and R$^z$ are defined in II below), but independently selected from R$^a$ and from each other if more than one R$^c$ is present, and is attached to a carbon ring atom or a nitrogen heteroatom the valency of which is not satisfied by the ring bonds;

p is 0 or 1;

b) 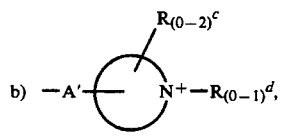

where

is a 5- or 6-membered monocyclic heterocycle or an 8-, 9- or 10-membered bicyclic heterocycle, the heterocycle containing a first nitrogen in an aromatic 5- or 6-membered first ring, with said first nitrogen quaternary by virtue of a substituent R$^d$ in addition to the ring bonds thereto, with said first nitrogen neutral in the absence of a substituent $R^d$, with attachment of the heterocycle to A' by way of a carbon atom of a ring, with the first ring containing 0 or 1 of either O or S, with the first ring containing 0 to 2 additional nitrogen atoms, with the first ring optionally fused to a 3- or 4-membered moiety to form the optional second ring, with the moiety containing at least one carbon atom, with the moiety containing 0 or 1 of either O or S, with the moiety containing 0 to 2 nitrogen atoms, and with the moiety being saturated or unsaturated and the second ring aromatic or non-aromatic;

$R^c$ is defined above;

$R^d$ is hydrogen, $NH_2$, $O^-$ or $C_1$–$C_4$alkyl (where the alkyl group is optionally mono-substituted with $R^q$ as defined under IIc below);

A' is $(CH_2)_m$—Q—$(CH_2)_n$, where m is 0 to 6 and n is 0 to 6 and Q is given above;

c) 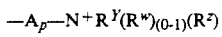

where $R^Y$ and $R^z$ are as defined under II below, $R^Y$ and $R^z$ may further be together a $C_2$–$C_4$ alkylidene radical to form a ring (optionally mono-substituted with $R^q$ as defined below) interrupted by $N(O)R^e$ or $N^+(R^e)_2$ (where $R^e$ is hydrogen, $C_1$–$C_4$alkyl, or $C_1$–$C_4$alkyl substituted with $R^q$ defined below), $R^w$ is hydrogen, $C_{1-4}$ alkyl, $O^-$, $NH_2$ or absent in which case the nitrogen is neutral, $R^w$, $R^y$ and $R^z$ may further together form a $C_5$–$C_{10}$ tertiary alkylidene radical which with $N^+$ forms a bicyclic ring, where the tertiary alkylidene radical is optionally mono-substituted with $R^q$ as defined below and where the tertiary carbon of the tertiary alkylidene radical is optionally replaced with nitrogen, $N^+R^e$ (where $R^e$ is defined above), or $N^+$—$O^-$, p is 0 or 1, and A is as defined above;

d) 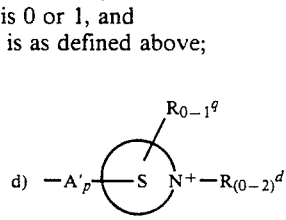

where

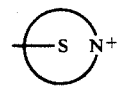

is a 5- or 6-membered monocyclic heterocycle or an 8-, 9- or 10-membered bicyclic heterocycle, the heterocycle containing a first nitrogen in a first ring, with the first ring saturated or unsaturated and non-aromatic, with the first nitrogen quaternary by virtue of one or two substituents $R^d$ in addition to the ring bonds thereto, with the first nitrogen alternatively neutral by virtue of zero or one substituents $R^d$ in addition to the ring bonds thereto, with attachment of the heterocycle to A' by way of a carbon atom or non-quaternary nitrogen atom of a ring, with the first ring containing in addition to carbon and the first nitrogen 0 to 1 of a member selected from the group consisting of the non-quaternary nitrogen of attachment, O, S, S(O), $S(O)_2$ and $NR^e$ where $R^e$ is defined above, with the first ring optionally fused to a 2-, 3- or 4-membered moiety to form the optional second ring, with the moiety optionally containing in addition to carbon the non-quaternary nitrogen of attachment, and with the moiety saturated or unsaturated and the second ring non-aromatic;

$R^d$ is defined above and where more than one $R^d$ is present on a nitrogen, at least one $R^d$ is hydrogen or $C_1$–$C_4$alkyl;

A' is defined above; and p is defined above;

$R^q$ is defined below;

II.

a) a trifluoromethyl group: —$CF_3$;

b) a halogen atom: —Br, —Cl, —F, or —I;

c) $C_1$–$C_4$ alkoxy radical: —$OC_{1-4}$ alkyl, wherein the alkyl is optionally mono-substituted by $R^q$, where $R^q$ is a member selected from the group consisting of —OH, —$OCH_3$, —CN, —$C(O)NH_2$, —$OC(O)NH_2$, CHO, —$OC(O)N(CH_3)_2$, —$SO_2NH_2$, —$SO_2N(CH_3)_2$, —$SOCH_3$, —$SO_2CH_3$, —F, —$CF_3$, —$COOM^a$ (where $M^a$ is hydrogen, alkali metal, methyl or phenyl), tetrazolyl (where the point of attachment is the carbon atom of the tetrazole ring and one of the nitrogen atoms is mono-substituted by $M^a$ as defined above) and —$SO_3M^b$ (where $M^b$ is hydrogen or an alkali metal);

d) a hydroxy group: —OH;

e) a carbonyloxy radical: —$O(C=O)R^s$, where $R^s$ is $C_{1-4}$ alkyl or phenyl, each of which is optionally mono-substituted by $R^q$ as defined above or tri-substituted with —F;

f) a carbamoyloxy radical; —$O(C=O)N(R^y)R^z$ where $R^y$ and $R^z$ are independently H, $C_{1-4}$ alkyl (optionally mono-substituted by $R^q$ as defined above), together a 3- to 5-membered alkylidene radical to form a ring (optionally substituted with $R^q$ as defined above) or together a 2- to 4-membered alkylidene radical, interrupted by —O—, —S—, —S(O)— or —$S(O)_2$—, to form a ring (where the ring is optionally mono-substituted with Rq as defined above);

g) a sulfur radical: —$S(O)_n$—$R^s$ where n = 0–2, and $R^s$ is defined above;

h) a sulfamoyl group: —$SO_2N(R^y)R^z$ where $R^y$ and $R^z$ are as defined above;

i) azido: $N_3$ j) a formamido group: —$N(R^t)(C=O)H$, where $R^t$ is H or $C_{1-4}$ alkyl, and the alkyl thereof is optionally mono-substituted by $R^q$ as defined above;

k) a ($C_1$–$C_4$ alkyl)carbonylamino radical: —$N(R^t)(C=O)C_{1-4}$ alkyl, where $R^t$ is as defined above, and the alkyl group is also optionally mono-substituted by $R^q$ as defined above;

l) a ($C_1$–$C_4$ alkoxy) carbonylamino radical: —$N(R^t)(C=O)OC_{1-4}$ alkyl, where $R^t$ is as defined above, and the alkyl group is also optionally mono-substituted by $R^q$ as defined above;

m) a ureido group: —$N(R^t)(C=O)N(R^y)R^z$ where $R^t$, $R^y$ and $R^z$ are as defined above;

n) a sulfonamido group: —$N(R^t)SO_2R^s$, where $R^s$ and $R^t$ are as defined above;

o) a cyano group: —CN;

p) a formyl or acetalized formyl radical: —(C=O)H or —$CH(OCH_3)_2$;

q) ($C_1$-$C_4$ alkyl)carbonyl radical wherein the carbonyl is acetalized: —$C(OCH_3)_2C_{1-4}$ alkyl, where the alkyl is optionally mono-substituted by $R^q$ as defined above;

r) carbonyl radical: —$(C=O)R^s$, where $R^s$ is as defined above;

s) a hydroximinomethyl radical in which the oxygen or carbon atom is optionally substituted by a $C_1$-$C_4$ alkyl group: —$(C=NOR^z)R^y$ where $R^y$ and $R^z$ are as defined above, except they may not be joined together to form a ring;

t) a ($C_1$-$C_4$ alkoxy)carbonyl radical: —$(C=O)OC_{1-4}$ alkyl, where the alkyl is optionally mono-substituted by $R^q$ as defined above;

u) a carbamoyl radical: —$(C=O)N(R^y)R^z$ where $R^y$ and $R^z$ are as defined above;

v) an N-hydroxycarbamoyl or N($C_1$-$C_4$ alkoxy)carbamoyl radical in which the nitrogen atom may be additionally substituted by a $C_1$-$C_4$ alkyl group: —$(C=O)$—$N(OR^y)R^z$ where $R^y$ and $R^z$ are as defined above, except they may not be joined together to form a ring;

w) a thiocarbamoyl group: —$(C=S)N(R^y)(R^z)$ where $R^y$ and $R^z$ are as defined above;

x) carboxyl: —$COOM^b$, where $M^b$ is as defined above;

y) thiocyanate: —SCN;

z) trifluoromethylthio: —$SCF_3$;

aa) tetrazolyl, where the point of attachment is the carbon atom of the tetrazole ring and one of the nitrogen atoms is mono-substituted by hydrogen, an alkali metal or a $C_1$-$C_4$ alkyl optionally substituted by $R^q$ as defined above;

ab) an anionic function selected from the group consisting of: phosphono [$P=O(OM^b)_2$]; alkylphosphono $\{P=O(OM^b)$—$[O(C_1$-$C_4$ alkyl)]\}$; alkylphosphinyl [$P=O(OM^b)$—$(C_1$-$C_4$alkyl)]; phosphoramido [$P=O(OM^b)N(R^y)R^z$ and $P=O(OM^b)NHR^x$]; sulfino ($SO_2M^b$); sulfo ($SO_3M^b$); acylsulfonamides selected from the structures $CONM^bSO_2R^x$, $CONM^bSO_2N(R^y)R^z$, $SO_2NM^bCON(R^y)R^z$; and $SO_2NM^bCN$, where $R^x$ is phenyl or heteroaryl, where heteroaryl is a monocyclic aromatic hydrocarbon group having 5 or 6 ring atoms, in which a carbon atom is the point of attachment, in which one of the carbon atoms has been replaced by a nitrogen atom, in which one additional carbon atom is optionally replaced by a heteroatom selected from O or S, and in which from 1 to 2 additional carbon atoms are optionally replaced by a nitrogen heteroatom, and where the phenyl and heteroaryl are optionally mono-substituted by $R^q$, as defined above; $M^b$ is as defined above; and $R^y$ and $R^z$ are as defined above;

ac) $C_5$-$C_7$ cycloalky group in which one of the carbon atoms in the ring is replaced by a heteroatom selected from O, S, NH or N($C_1$-$C_4$ alkyl) and in which one additional carbon atom may be replaced by NH or N($C_1$-$C_4$ alkyl), and in which at least one carbon atom adjacent to each nitrogen heteroatom has both of its attached hydrogen atoms replaced by one oxygen thus forming a carbonyl moiety and there are one or two carbonyl moieties present in the ring;

ad) $C_2$-$C_4$ alkenyl radical, optionally mono-substituted by one of the substituents a) to ac) above and phenyl which is optionally substituted by $R^q$ as defined above;

ae) $C_2$-$C_4$ alkynyl radical, optionally mono-substituted by one of the substituents a) to ac) above;

af) $C_1$-$C_4$ alkyl radical;

ag) $C_1$-$C_4$ alkyl mono-substituted by one of the substituents a) -ac) above;

ah) a 2-oxazolidinonyl moiety in which the point of attachment is the nitrogen atom of the oxazolidinone ring, the ring oxygen atom is optionally replaced by a heteroatom selected from —S— and $NR^t$ (where $R^t$ is as defined above) and one of the saturated carbon atoms of the oxazolidinone ring is optionally mono-substituted by one of the substituents a) to ag) above; and M is selected from:
   i) hydrogen;
   ii) a pharmaceutically acceptable esterifying group or removable carboxyl protecting group;
   iii) an alkali metal or other pharmaceutically acceptable cation; or
   iv) a negative charge which is balanced by a positively charged group.

2. A compound according to claim 1 wherein $R^1$ is hydrogen and $R^2$ is (R)—$CH_3CH(OH)$— or (R)—$CH_3CH(F)$—.

3. The compound of claim 2 wherein said Type I.a. substituents are selected from the group consisting of:

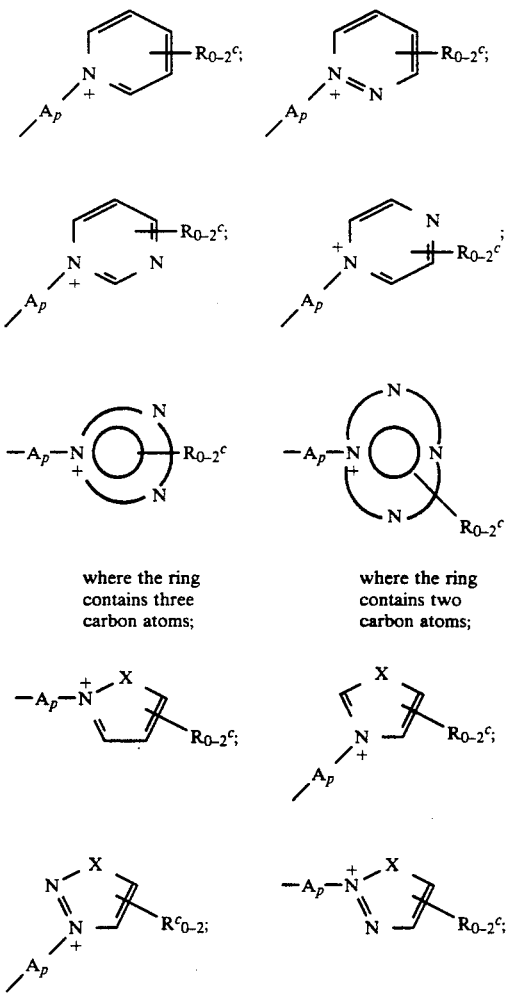

where the ring contains three carbon atoms;

where the ring contains two carbon atoms;

-continued
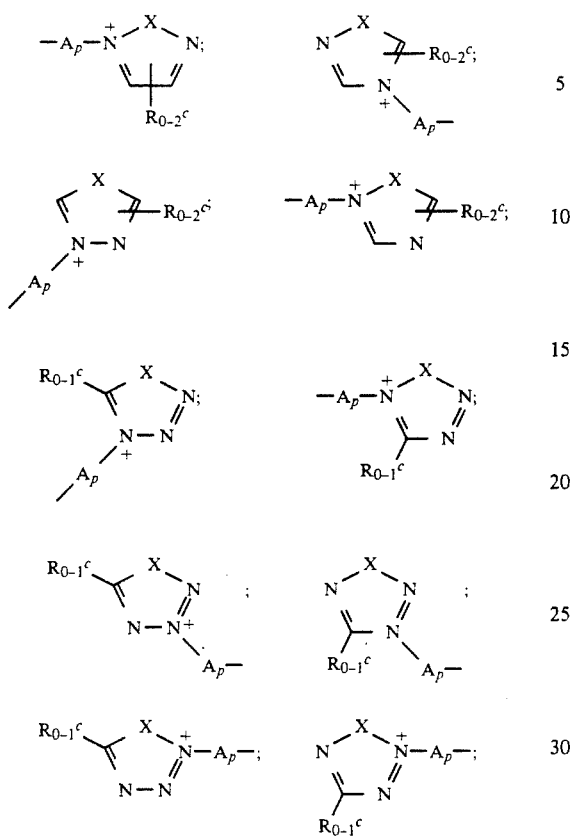
where X=O, S, or NR$^c$.
4. The compound of claim 2 wherein said Type I.b. substituents are selected from the group consisting of:
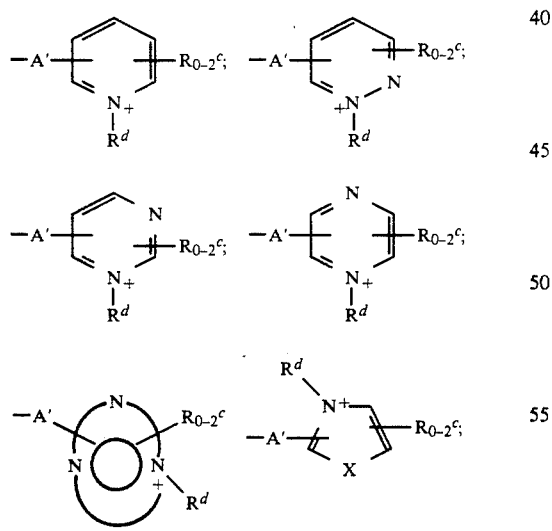
where the ring contains three carbon atoms;
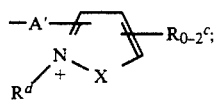
-continued
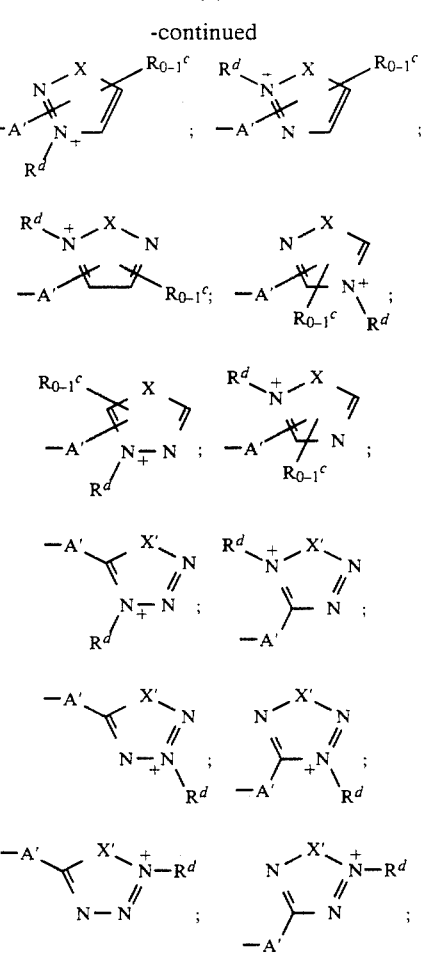
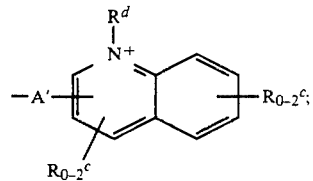
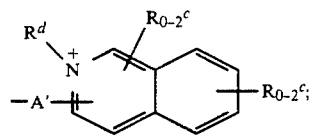
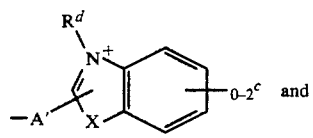
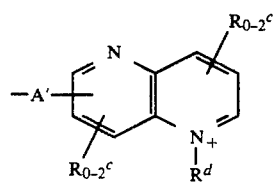
where X=O, S, or NR$^c$ and X'=O or S.
5. The compound of claim 2 wherein said Type I.c. substituents are selected from the group consisting of:

$-A_p-^+N(CH_3)_3$, $-A_p-^+N(CH_2CH_3)_3$, $-A_p-^+N(CH_3)_2CH_2R^q$, $-A_p-^+N(CH_2CH_3)_2CH_2CH_2R^q$,

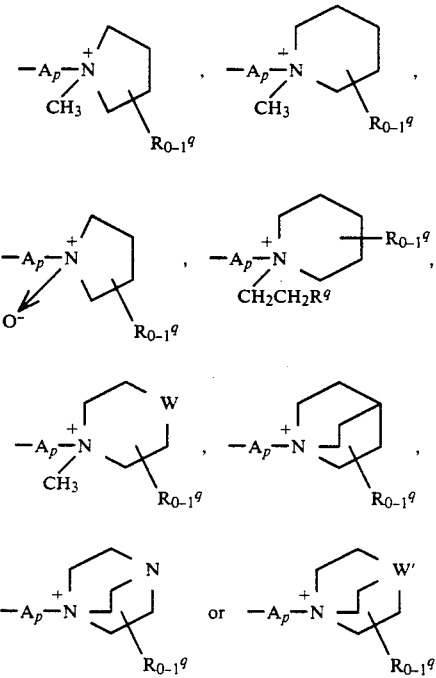

where W is O, S, NR$^e$, N(O)R$^e$, SO, SO$_2$ or N$^+$(R$^e$)$_2$ and W' is N$^+$R$^e$ or NO.

6. The compound of claim 2 wherein said Type I.d. substituents are selected from the group consisting of:

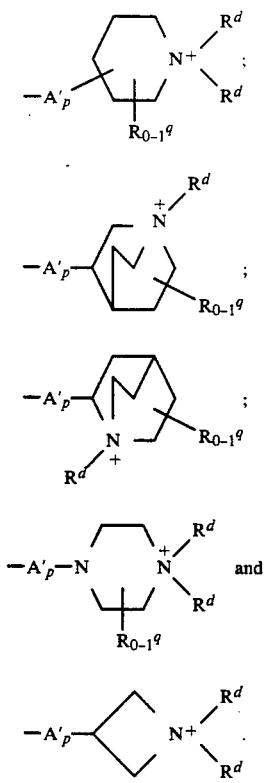

7. The compound of claim 2 wherein said R$^c$ where attached to a ring carbon atom is selected from the group consisting of —NH$_2$, —SCH$_3$, —SOCH$_3$, —CH$_2$OH, —(CH$_2$)$_2$OH, —OCH$_3$, —COOM$^b$, —CH$_2$COOM$^b$, —CH$_2$CH$_2$COOM$^b$, —CH$_2$SOCH$_3$, —CH$_2$SCH$_3$, —SO$_3$M$^b$, —CH$_2$SO$_3$M$^b$, —CH$_2$CH$_2$SO$_3$M$^b$, —Br, —Cl, —F, —I, —CH$_3$, CH$_2$CH$_3$, CH$_2$CONH$_2$ and CH$_2$CON(C$_1$-C$_4$alkyl) where M$^b$ is defined above.

8. The compound of claim 2 wherein said R$^c$ where attached to a neutral ring nitrogen atom is selected from the group consisting of —CH$_2$OH, —(CH$_2$)$_2$OH, —CH$_2$COOM$^b$, —CH$_2$CH$_2$COOM$^b$, —CH$_2$SOCH$_3$, —CH$_2$SCH$_3$, —CH$_2$SO$_3$M$^b$, —CH$_2$CH$_2$SO$_3$M$^b$, —CH$_3$, CH$_2$CH$_3$, CH$_2$CONH$_2$ and CH$_2$CON(C$_1$-C$_4$alkyl) where M$^b$ is defined above.

9. The compound of claim 2 wherein R$^d$ is selected from the group consisting of hydrogen, —CH$_3$, CH$_2$CH$_3$, —CH$_2$CH$_2$CH$_3$, —CH$_2$COOM$^b$, —CH$_2$SO$_3$M$^b$, —NH$_2$ and O$^{(-)}$, where M$^b$ is defined above.

10. The compound of claim 2 wherein A is selected from the group consisting of —CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —CONHCH$_2$CH$_2$—, —SO$_2$NHCH$_2$CH$_2$—, —COCH$_2$—, —CH=CHCH$_2$— and —CH$_2$OCH$_2$CH$_2$—.

11. The compound of claim 2 wherein A' is selected from the group consisting of —CH$_2$—, —CH$_2$CH$_2$—, —CH$_2$CH$_2$CH$_2$—, —CH$_2$CH$_2$CH$_2$CH$_2$—, —OCH$_2$CH$_2$—, —SOCH$_2$—, —SO$_2$CH$_2$—, —SCH$_2$CH$_2$—, —SOCH$_2$CH$_2$—, —SO$_2$CH$_2$CH$_2$—, —NHCH$_2$CH$_2$—, —N(CH$_3$)CH$_2$CH$_2$—, —CH$_2$N(CH$_3$)CH$_2$CH$_2$—, —CONHCH$_2$CH$_2$—, —SO$_2$NHCH$_2$CH$_2$—, —COCH$_2$—, —CH=CHCH$_2$—, —CH$_2$OCH$_2$CH$_2$—, —O—, —S—, —NH—, —SO$_2$—, —SO$_2$NH—, —CONH—, —CH=CH—, —CH$_2$S—, —CH$_2$NH—, —CONHCH$_2$— and —SO$_2$NHCH$_2$—.

12. The compound of claim 2 wherein said R$^a$ substituents of Type II are selected from the group consisting of:

| | |
|---|---|
| —OCH$_3$ | —OCH$_2$CO$_2$CH$_3$ |
| —OCH$_2$CH$_2$OH | —CF$_3$ |
| —F | —Cl |
| —Br | —I |
| —OH | —OCOCH$_3$ |
| —OCONH$_2$ | —SCH$_3$ |
| —SOCH$_3$ | —SO$_2$CH$_3$ |
| —SCH$_2$CH$_2$OH | —SOCH$_2$CH$_2$OH |
| —SO$_2$NH$_2$ | —SO$_2$N(CH$_3$)$_2$ |
| —NHCHO | —NHCOCH$_3$ |
| —NHCO$_2$CH$_3$ | —NHSO$_2$CH$_3$ |
| —CN | —CHO |
| —COCH$_3$ | —COCH$_2$OH |
| —CH=NOH | —CH=NOCH$_3$ |
| —CH=NOCH$_2$CO$_2$CH$_3$ | —CH=NOCMe$_2$CO$_2$CH$_3$ |
| —CH=NOCMe$_2$CONH$_2$ | —CO$_2$CH$_2$CH$_2$OH |
| —CONH$_2$ | —CONHCH$_3$ |
| —CON(CH$_3$)$_2$ | —CONHCH$_2$CN |
| —CONHCH$_2$CONH$_2$ | —CONHCH$_2$CO$_2$CH$_3$ |
| —CONHOH | —CONHOCH$_3$ |
| —tetrazolyl | —CO$_2$CH$_3$ |
| —SCF$_3$ | —CONHSO$_2$Ph |
| —CONHSO$_2$NH$_2$ | —SO$_2$CF$_3$ |
| —SO$_2$NHCN | —SO$_2$NHCONH$_2$ |
| —CH=CHCN | —CH=CHCONH$_2$ |
| —CH=CHCO$_2$CH$_3$ | —C≡C—CONH$_2$ |
| —C≡C—CN | —CH$_2$OH |
| —CH$_2$N$_3$ | —CH$_2$CO$_2$CH$_3$ |

-continued

| | |
|---|---|
| —SO$_2$CH$_2$CH$_2$OH | —CH$_2$CONH$_2$ and |
| —CH$_2$I. | |

13. The compounds of claim 2 having the formula:

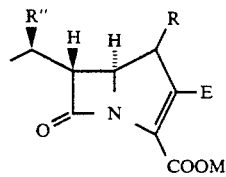

where R″ is F or OH, R is H or Me and E is:

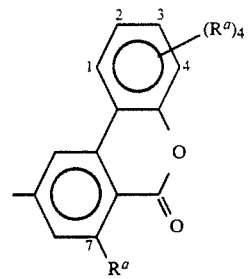 or 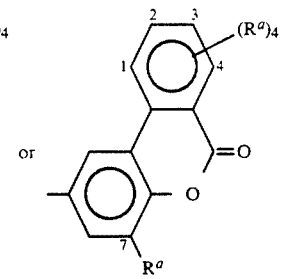

and wherein M and R$^a$ are selected from the group consisting of:

| M | R$^a$ | Position |
|---|---|---|
| (−) | —CH$_2$N$^+$ ⟨pyridyl⟩-NH$_2$ | 7 |
| (−) | —CH$_2$N$^+$ ⟨pyridyl⟩-NH$_2$ | 3 |
| (−) | —CH$_2$N$^+$ ⟨pyridyl⟩-NH$_2$ | 4 |
| (−) | —CH$_2$N$^+$ ⟨pyridyl⟩-NH$_2$ | 2 |
| (−) | —CH$_2$N$^+$ ⟨pyridyl⟩-NH$_2$ | 3 |
| (−) | —CH$_2$N$^+$ ⟨pyridyl⟩-NH$_2$ | 7 |
| (−) | —CH$_2$N$^+$ ⟨pyridyl⟩-NH$_2$ | 3 |
| (−) | —CH$_2$N$^+$ ⟨pyridyl⟩-NH$_2$ | 4 |
| (−) | —CH$_2$N$^+$ ⟨pyridyl⟩-NH$_2$ | 2 |

-continued

| | | |
|---|---|---|
| (−) | −CH₂N⁺=CH-CH=C(NH₂)-CH=CH (pyridinium-4-amine) | 1 |
| (−) | −CH₂N⁺(imidazolium)-N-CH₃ | 7 |
| (−) | −CH₂N⁺(imidazolium)-N-CH₃ | 3 |
| (−) | −CH₂N⁺(imidazolium)-N-CH₃ | 4 |
| (−) | −CH₂N⁺(imidazolium)-N-CH₃ | 2 |
| (−) | −CH₂N⁺(triazolium)-N-CH₃ | 3 |
| (−) | −N⁺(imidazolium)-N-CH₃ | 7 |
| (−) | −N⁺(pyridinium) | 7 |
| (−) | −CH₂N⁺(triazolium)-N-CH₃ | 4 |
| (−) | −CH₂N⁺(triazolium)-N-CH₃ | 7 |
| (−) | −CH₂N⁺(imidazolium)-NCH₂CONH₂ | 7 |
| (−) | −CH₂N⁺(pyrazolium)-N-CH₃ | 3 |
| (−) | −CH₂N⁺(imidazolium)-N-CH₂SOCH₃ | 4 |
| K | −CH₂N⁺(imidazolium)-NCH₂SO₃⁻ | 4 |
| (−) | −CH₂N⁺(triazolium)-NCH₃ | 3 |

-continued
| | | |
|---|---|---|
| K | 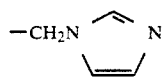 | 3 |
| K | 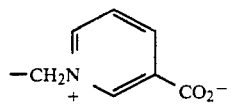 | 3 |
| (−) | 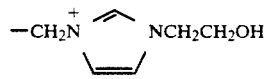 | 4 |
| (−) | 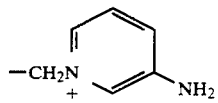 | 4 |
| (−) | 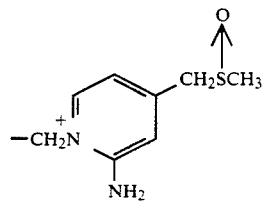 | 3 |
| (−) | 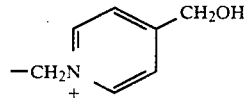 | 3 |
| (−) | 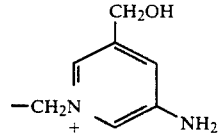 | 4 |
| (−) | 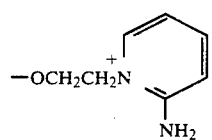 | 7 |
| (−) | 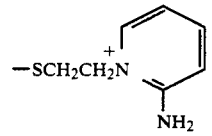 | 7 |
| (−) | 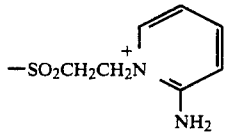 | 7 |
| (−) | 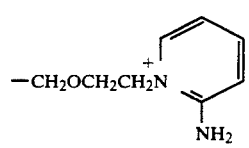 | 4 |

-continued
| | | |
|---|---|---|
| (—) | 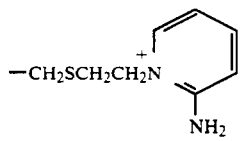 | 4 |
| (—) | 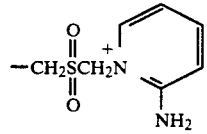 | 4 |
| (—) | 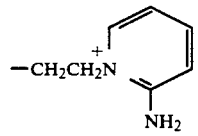 | 1 |
| (—) | 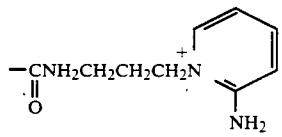 | 7 |
| (—) | 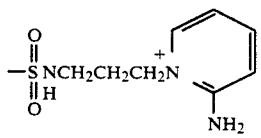 | 4 |
| (—) | 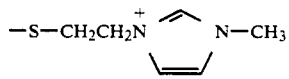 | 7 |
| (—) | 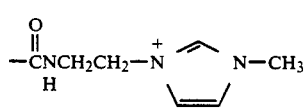 | 3 |
| (—) | 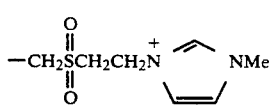 | 3 |
| (—) | 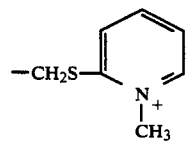 | 3 |
| (—) | 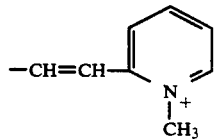 | 3 |
| H | 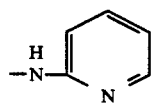 | 3 |

| | | |
|---|---|---|
| (−) | 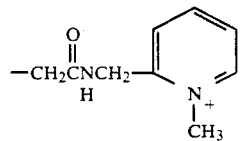 | 3 |
| (−) | 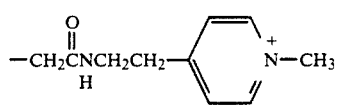 | 3 |
| (−) | 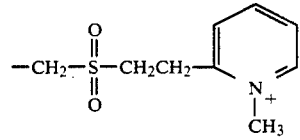 | 3 |
| (−) | 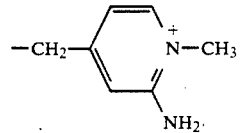 | 3 |
| (−) | 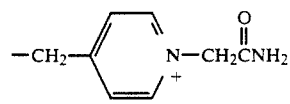 | 2 |
| K | 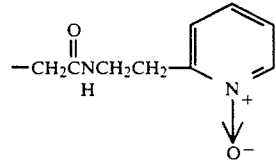 | 3 |
| K | 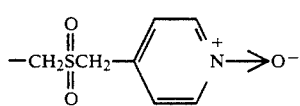 | 3 |
| (−) | 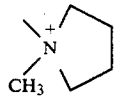 | 7 |
| (−) | 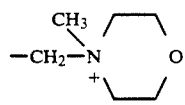 | 3 |
| (−) | 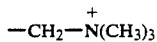 | 4 |
| (−) | 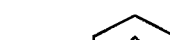 | 4 |
| K | 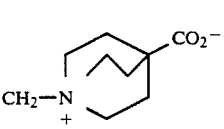 | 4 |

-continued
| | | | | |
|---|---|---|---|---|
| K | 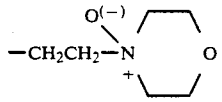 | 3 | | |
| (−) | 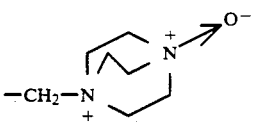 | 3 | | |
| (−) | 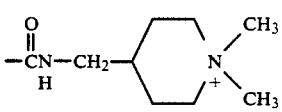 | 7 | | |
| M | $R^a$ | $R^a$ Position | $R^a$ | $R^a$ Position |
|---|---|---|---|---|
| (−) | CN | 7 | 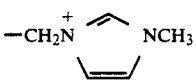 | 3 |
| (−) | SOCH$_3$ | 7 | 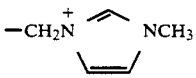 | 3 |
| (−) | CO$_2$K | 7 | 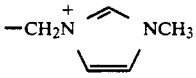 | 3 |
| (−) | SO$_3$K | 7 | 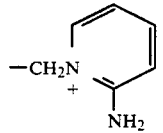 | 3 |
| (−) |  | 7 | 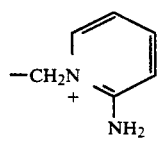 | 4 |
| (−) | SO$_2$CH$_3$ | 7 | 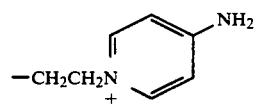 | 4 |
| (−) | CN | 7 | 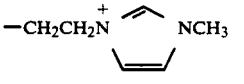 | 4 |
| (−) | CONH$_2$ | 7 | 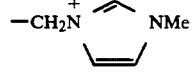 | 3 |
| (−) | CONH$_2$ | 7 | 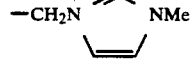 | 4 |
| (−) | 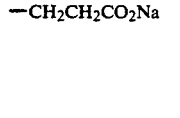 | 7 | —CH$_2$CH$_2$CO$_2$Na | 3 |

| | | | | |
|---|---|---|---|---|
| Na | CN | 7 | —CH₂—N⟨imidazole⟩ | 3 |
| (−) | SO₃K | 3 | —CH₂CH₂N⁺(pyrrolidine)CH₃ | 4 |
| (−) | CHO | 7 | —CH₂N⁺(2-aminopyridine) | 3 |

14. A compound according to claim 2 wherein at least $R^a$ in the 3-, 4- or 7-position is other than hydrogen.

15. A compound according to claim 2 wherein there are, in total, up to two $R^a$ substituents other than hydrogen.

16. A composition comprising a pharmaceutically acceptable carrier and from 0.1% to about 99% by weight of active material of claim 1.

17. A composition according to claim 16 which further comprises an inhibitorily effective amount of a DHP inhibitor.

18. A composition according to claim 17 wherein said DHP inhibitor is 7-(L-2-amino-2-carboxyethylthio)-2-(2,2-dimethylcyclopropanecarboxamide)-2-heptanoic acid.

19. A method for treating bacterial infection in mammals comprising administering an effective amount of a compound of claim 1 and a pharmaceutically acceptable carrier therefor.

20. A method according to claim 19 which further comprises administering an inhibitorily effective amount of a DHP inhibitor.

21. A method according to claim 20 wherein said DHP inhibitor is 7-(L-2-amino-2-carboxyethylthio)-2-(2,2-dimethylcyclopropanecarboxamide)-2-heptanoic acid.

22. A compound selected from the group consisting of:

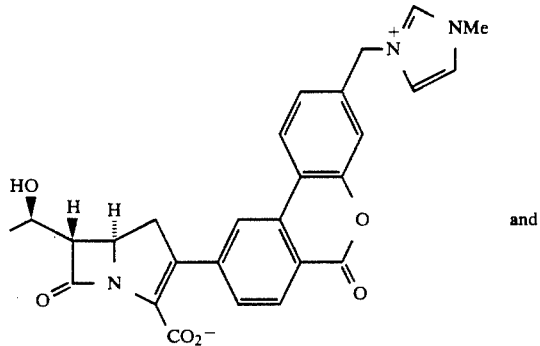

and

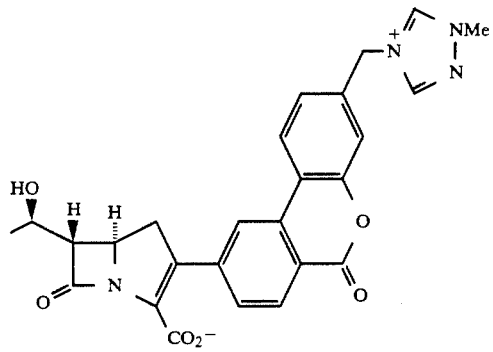

* * * * *